(12) United States Patent
Chernyak et al.

(10) Patent No.: US 10,098,783 B2
(45) Date of Patent: Oct. 16, 2018

(54) TILT COMPENSATION, MEASUREMENT, AND ASSOCIATED ADJUSTMENT OF REFRACTIVE PRESCRIPTIONS DURING SURGICAL AND OTHER TREATMENTS OF THE EYE

(71) Applicant: AMO Development, LLC, Santa Ana, CA (US)

(72) Inventors: Dimitri Chernyak, Sunnyvale, CA (US); Anatoly Fabrikant, Fremont, CA (US)

(73) Assignee: AMO Development, LLC, Santa Ana, CA (US)

( * ) Notice: Subject to any disclaimer, the term of this patent is extended or adjusted under 35 U.S.C. 154(b) by 15 days.

(21) Appl. No.: 14/618,163

(22) Filed: Feb. 10, 2015

(65) Prior Publication Data

US 2015/0157499 A1 Jun. 11, 2015

Related U.S. Application Data

(62) Division of application No. 13/188,323, filed on Jul. 21, 2011, now Pat. No. 8,978,660.

(51) Int. Cl.
*A61B 18/20* (2006.01)
*A61F 9/008* (2006.01)

(52) U.S. Cl.
CPC .......... *A61F 9/008* (2013.01); *A61F 9/00804* (2013.01); *A61F 2009/00844* (2013.01); *A61F 2009/00846* (2013.01); *A61F 2009/00848* (2013.01); *A61F 2009/00872* (2013.01); *A61F 2009/00882* (2013.01)

(58) Field of Classification Search
CPC .. A61F 9/008; A61F 9/00802; A61F 9/00804; A61F 9/00814; A61F 2009/00848; A61F 2009/00872; A61F 2009/00878; A61F 2009/00882
USPC ....... 606/4–6, 10–12; 351/205–212; 128/898
See application file for complete search history.

(56) References Cited

U.S. PATENT DOCUMENTS

| | | | |
|---|---|---|---|
| 4,665,913 A | 5/1987 | L'Esperance, Jr. |
| 4,669,466 A | 6/1987 | L'Esperance |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 5,108,388 A | 4/1992 | Trokel |
| 5,163,934 A | 11/1992 | Munnerlyn |

(Continued)

FOREIGN PATENT DOCUMENTS

WO 0124719 A1 4/2001

*Primary Examiner* — Ahmed Farah
(74) *Attorney, Agent, or Firm* — Johnson & Johnson Surgical Vision, Inc.

(57) ABSTRACT

Embodiments of the present invention provide methods and systems for determining an ablation treatment for an eye of a patient. The systems and method may involve determining an ellipsoid shape corresponding to an anterior corneal surface of the patient's eye. The ellipsoid shape may include an anterior portion, a major axis, and an apex, where the major axis intersects the anterior portion at the apex. The systems and method may also involve determining a tilted orientation of the eye, such as when the patient fixates on a target during a laser ablation procedure. The systems and method may further involve determining the ablation treatment based on the ellipsoid shape and/or the tilted orientation.

18 Claims, 21 Drawing Sheets

(56) References Cited

U.S. PATENT DOCUMENTS

| | | | |
|---|---|---|---|
| 5,207,668 A | 5/1993 | L'Esperance, Jr. | |
| 5,219,343 A | 6/1993 | L'Esperance, Jr. | |
| 5,219,344 A | 6/1993 | Yoder, Jr. | |
| 5,646,791 A | 7/1997 | Glockler | |
| 5,683,379 A | 11/1997 | Hohla | |
| 5,713,892 A | 2/1998 | Shimmick | |
| 5,777,719 A | 7/1998 | Williams et al. | |
| 5,807,379 A | 9/1998 | L'Esperance, Jr. | |
| 5,886,767 A * | 3/1999 | Snook | A61B 3/107 351/211 |
| 6,004,313 A | 12/1999 | Shimmick et al. | |
| 6,090,100 A * | 7/2000 | Hohla | A61F 9/008 606/10 |
| 6,203,539 B1 | 3/2001 | Shimmick et al. | |
| 6,271,915 B1 | 8/2001 | Frey et al. | |
| 6,315,413 B1 | 11/2001 | Shimmick et al. | |
| 6,331,177 B1 | 12/2001 | Munnerlyn et al. | |
| 6,394,999 B1 | 5/2002 | Williams et al. | |
| 6,530,916 B1 | 3/2003 | Shimmick | |
| 6,572,606 B2 | 6/2003 | Kliewer et al. | |
| 6,610,048 B1 * | 8/2003 | Holladay | A61B 3/0025 606/5 |
| 6,923,802 B2 | 8/2005 | Williams et al. | |
| 7,130,835 B2 | 10/2006 | Cox et al. | |
| 7,419,485 B2 | 9/2008 | Chernyak | |
| 7,544,194 B2 | 6/2009 | Mrochen et al. | |
| 8,057,037 B2 | 11/2011 | Dai | |
| 8,260,008 B2 * | 9/2012 | Hanna | G06K 9/00604 382/100 |
| 8,878,749 B1 * | 11/2014 | Wu | G01S 17/06 345/8 |
| 8,978,660 B2 | 3/2015 | Chernyak et al. | |
| 2002/0075451 A1 * | 6/2002 | Ruiz | A61F 9/008 351/212 |
| 2002/0115988 A1 * | 8/2002 | Holladay | A61B 3/0025 606/5 |
| 2002/0183772 A1 | 12/2002 | Lieberman et al. | |
| 2002/0198516 A1 * | 12/2002 | Knopp | B23K 26/04 606/5 |
| 2005/0195364 A1 | 9/2005 | Dai | |
| 2009/0018532 A1 * | 1/2009 | Salin | A61F 9/00827 606/5 |
| 2010/0114078 A1 * | 5/2010 | Grierson | A61F 2/14 606/5 |
| 2010/0179793 A1 | 7/2010 | Chernyak et al. | |
| 2011/0134391 A1 | 6/2011 | Dai et al. | |
| 2014/0232988 A1 * | 8/2014 | Kersting | A61B 3/1005 351/206 |

* cited by examiner

SPHERICAL ABERRATION AND COMA CAUSED BY ASSYMETRY OF THE COSINE EFFECT DUE TO EYE TILTS

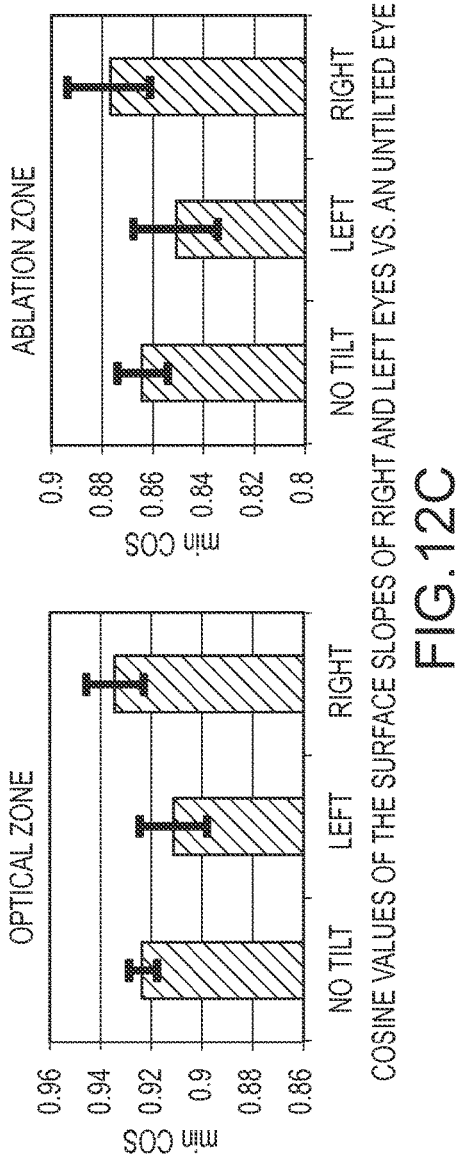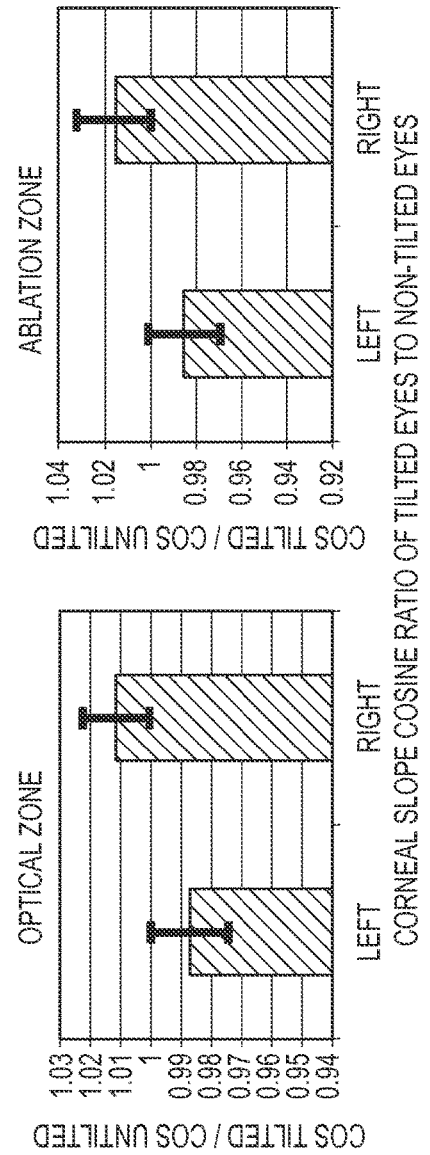
FIG. 12C
FIG. 12D

TILT COMPENSATION, MEASUREMENT, AND ASSOCIATED ADJUSTMENT OF REFRACTIVE PRESCRIPTIONS DURING SURGICAL AND OTHER TREATMENTS OF THE EYE

CROSS-REFERENCE TO RELATED APPLICATIONS

This application is a divisional of and claims the benefit of priority to U.S. Nonprovisional patent application Ser. No. 13/188,323 filed Jul. 21, 2011, now U.S. Pat. No. 8,978,660, issued on Mar. 17, 2015, the entire contents of which incorporated herein by reference for all purposes.

BACKGROUND OF THE INVENTION

Embodiments of the present invention are generally related to determining ablation treatments for laser eye treatment surgery. The invention provides systems and methods for determining ablation treatments based on a tilted orientation of a patient's eye.

Known laser eye surgery procedures generally employ an ultraviolet or infrared laser to remove a microscopic layer of stromal tissue from the cornea of the eye. Examples of laser eye surgery procedures include photorefractive keratectomy (PRK), phototherapeutic keratectomy (PTK), laser assisted in situ keratomileusis (LASIK), laser epithelial keratomileusis (LASEK), and the like. A laser typically removes a selected shape of a corneal tissue, often to correct refractive errors of an eye. Ultraviolet laser ablation results in photo-decomposition of a corneal tissue, but generally does not cause significant thermal damage to adjacent and underlying tissues of an eye. Irradiated molecules are broken into smaller volatile fragments photochemically, directly breaking intermolecular bonds.

Laser ablation procedures can remove a targeted amount stroma of a cornea to change a cornea's contour for varying purposes, such as for correcting myopia, hyperopia, astigmatism, and the like. Control over a distribution of ablation energy across a cornea may be provided by a variety of systems and methods, including use of ablatable masks, fixed and moveable apertures, controlled scanning systems, eye movement tracking mechanisms, and the like. In known systems, a laser beam often comprises a series of discrete pulses of laser light energy, with a total shape and amount of tissue removed being determined by a shape, size, location, and/or number of laser energy pulses impinging on a cornea. A variety of algorithms may be used to calculate the pattern of laser pulses used to reshape a cornea so as to correct a refractive error of an eye. Known systems make use of a variety of forms of lasers and laser energy to effect a correction, including infrared lasers, ultraviolet lasers, femtosecond lasers, wavelength multiplied solid-state lasers, and the like. Alternative vision correction techniques make use of radial incisions in a cornea, intraocular lenses, removable corneal support structures, and the like.

Known corneal correction treatment methods have generally been successful in correcting standard vision errors, such as myopia, hyperopia, astigmatism, and the like. By customizing an ablation pattern based on wavefront measurements, it may be possible to correct minor aberrations so as to reliably and repeatedly provide visual acuity greater than 20/20. Such detailed corrections will benefit from an extremely accurate ablation of tissue.

Known methods for calculation of a customized ablation pattern using wavefront sensor data generally involves mathematically modeling a surface of the cornea using expansion series techniques. More specifically, Zernike polynomials have been employed to model the corneal surface and refractive aberrations of the eye. Coefficients of a Zernike polynomial are derived through known fitting techniques, and an optical correction procedure is then determined using a shape indicated by a mathematical series expansion model.

Known methodology for determining laser ablation treatments based on wavefront sensor data and spectacles often provides real benefits to patients in need thereof. Yet further advancement in ablation technique technology, particularly for refractive correction purposes, is desired. Embodiments of the present invention provide solutions for at least some of these outstanding needs.

BRIEF SUMMARY OF THE INVENTION

Embodiments of the present invention provide systems and methods for vision treatment which take into account a detailed ablative interaction of a laser beam with a detailed anatomy of a tissue surface of an eye. Exemplary techniques may involve determining an ellipsoid shape corresponding to an anterior corneal surface of the patient's eye. The ellipsoid shape may include an anterior portion, a major axis, and an apex, where the major axis intersects the anterior portion at the apex. The systems and method may also involve determining a tilted orientation of the eye, such as when the patient fixates on a target during a laser ablation procedure. The systems and method may further involve determining the ablation treatment based on the ellipsoid shape and/or the tilted orientation.

In one aspect, embodiments of the present invention may include a method for determining an ablation treatment for an eye of a patient. The method may include determining an ellipsoid shape corresponding to an anterior corneal surface of the eye, the ellipsoid shape having an anterior portion, a major axis, and an apex such that the major axis intersects the anterior portion at the apex. The method may also include determining a tilted orientation of the eye when the patient fixates on a target during a laser ablation procedure and determining the ablation treatment based on the ellipsoid shape and the tilted orientation.

The tilted orientation may include the major axis rotationally offset from an axis of a laser beam path. In one embodiment, determining the tilted orientation may include determining a vertex of the ellipsoid where the vertex corresponds to a foremost point of the anterior corneal surface, and determining an offset between the apex and the vertex. In another embodiment, determining the tilted orientation may include obtaining a topography measurement of the anterior corneal surface and fitting the topography measurement on the ellipsoid shape to obtain the tilted orientation. In another embodiment, determining the ellipsoid shape may include determining a keratometry profile of the anterior corneal surface. The keratometry profile may include a first curvature value, a second curvature value, and a torsional rotational angle.

The tilted orientation may include a first tilt in a first direction and a second tilt in a second direction orthogonal to the first direction. The method may further include determining an energy level for a laser treatment device based on the ablation treatment and/or an ablation time for the laser treatment device based on the ablation treatment.

In another aspect, embodiments of the present invention may include a method for determining an ablation treatment for an eye of a patient. The method may include determining an ellipsoid model corresponding to an anterior corneal surface of the eye, the ellipsoid model having an anterior portion, a major axis, and an apex such that the major axis intersects the anterior portion at the apex. The method may also include calculating a nominal ablation pattern for the eye based on the ellipsoid model. The method may further include determining a tilted orientation of the eye when the patient fixates on a target during a laser ablation procedure; where determining the tilted orientation includes: determining a surface slope of the anterior corneal surface in a first direction extending radially from the apex; determining a surface slope of the anterior corneal surface in a second direction extending radially from the apex, where the surface slope in the first direction is steeper than the surface slope in the second direction; and determining the ablation treatment by adjusting the nominal ablation pattern based on the surface slope in the first direction and the surface slope in the second direction.

The nominal ablation pattern may be based on a surface slope of a non-tilted ellipsoid model. Determining the nominal ablation pattern may include calculating a cosine adjustment measure based on a non-tilted ellipsoid model and determining the ablation pattern may include adjusting the cosine adjustment measure based on an adjusted surface slope corresponding to the tilted orientation. Calculating the nominal ablation pattern may include applying a cosine adjustment measure to a wavefront guided treatment plan and adjusting the nominal ablation pattern may include adjusting the cosine adjustment measure based on the tilted orientation.

The method may additionally include determining a misalignment between an axis of a laser beam and a vertex of the ellipsoid model where the vertex corresponds to a foremost point of the anterior corneal surface, and adjusting the ablation pattern based on the misalignment.

In another aspect, embodiments of the present invention may include a computer program product for determining an ablation treatment for an eye of a patient. The program product may include code for accepting an ellipsoid shape corresponding to an anterior corneal surface of the eye where the ellipsoid shape has an anterior portion, a major axis, and an apex such that the major axis intersects the anterior portion at the apex. The program product may also include code for accepting a tilted orientation of the eye where the tilted orientation corresponds to a laser ablation procedure target fixation of the patient's eye. The program product may further include code for determining the ablation treatment based on the ellipsoid shape and the tilted orientation and a computer-readable medium for storing the codes.

In another aspect, embodiments of the present invention may include a machine-readable medium having machine-executable instructions configured to perform a method for determining an ablation treatment for an eye of a patient where the includes determining an ellipsoid shape corresponding to an anterior corneal surface of the eye, the ellipsoid shape having an anterior portion, a major axis, and an apex such that the major axis intersects the anterior portion at the apex. The method may also include determining a tilted orientation of the eye when the patient fixates on a target during a laser ablation procedure and determining the ablation treatment based on the ellipsoid shape and the tilted orientation.

The method may further include determining a misalignment between the axis of the laser beam and a vertex of the ellipsoid shape where the vertex corresponds to a foremost point of the anterior corneal surface, and may include adjusting the laser ablation pattern based on the misalignment. The method may additionally include determining an energy level for a laser treatment device based on the laser ablation pattern and/or determining an ablation time for the laser treatment device based on the laser ablation pattern. In some embodiments, the tilted orientation may include the major axis rotationally offset from an axis of a laser beam path.

In another aspect, embodiments of the present invention may include a system for determining an ablation treatment for an eye of a patient. The system may include a first input module comprising a tangible medium embodying machine-readable code that receives an ellipsoid shape corresponding to an anterior corneal surface of the eye where the ellipsoid shape includes an anterior portion, a major axis, and an apex such that the major axis intersects the anterior portion at the apex. The system may also include a second input module comprising a tangible medium embodying machine-readable code that receives a tilted orientation of the eye where the tilted orientation corresponds to a laser ablation procedure target fixation of the patient's eye. The system may further include a treatment module comprising a tangible medium embodying machine-readable code that that determines the ablation treatment based on the ellipsoid shape and the tilted orientation.

In another aspect, embodiments of the present invention may include a system for determining an ablation treatment for an eye of a patient. The system may include a laser ablation device that emits a laser beam to ablate at least a portion of the cornea of the patient's eye and a control device communicatively coupled with the laser ablation device and configured to control the laser ablation device according to the ablation treatment. The ablation treatment may be determined from a method including determining an ellipsoid shape corresponding to an anterior corneal surface of the eye where the ellipsoid shape has an anterior portion, a major axis, and an apex such that the major axis intersects the anterior portion at the apex. The method may also include determining a tilted orientation of the eye when the patient fixates on a target during a laser ablation procedure and determining the laser ablation treatment based on the ellipsoid shape and the tilted orientation.

The method may further include determining a misalignment between an axis of the laser beam and a vertex of the ellipsoid shape where the vertex corresponds to a foremost point of the anterior corneal surface and adjusting the laser ablation pattern based on the misalignment. Adjusting the laser ablation pattern based on the misalignment may include adjusting a cosine measure to account for the misalignment. The method may additionally include determining an energy level for the laser ablation device based on the laser ablation pattern and/or determining an ablation time for the laser ablation device based on the laser ablation pattern.

BRIEF DESCRIPTION OF THE DRAWINGS

FIGS. 12A-D provide various graphical illustrations associated with ablation treatment adjustment examples according to an embodiment of the present invention.

DETAILED DESCRIPTION OF THE INVENTION

Figure 1:
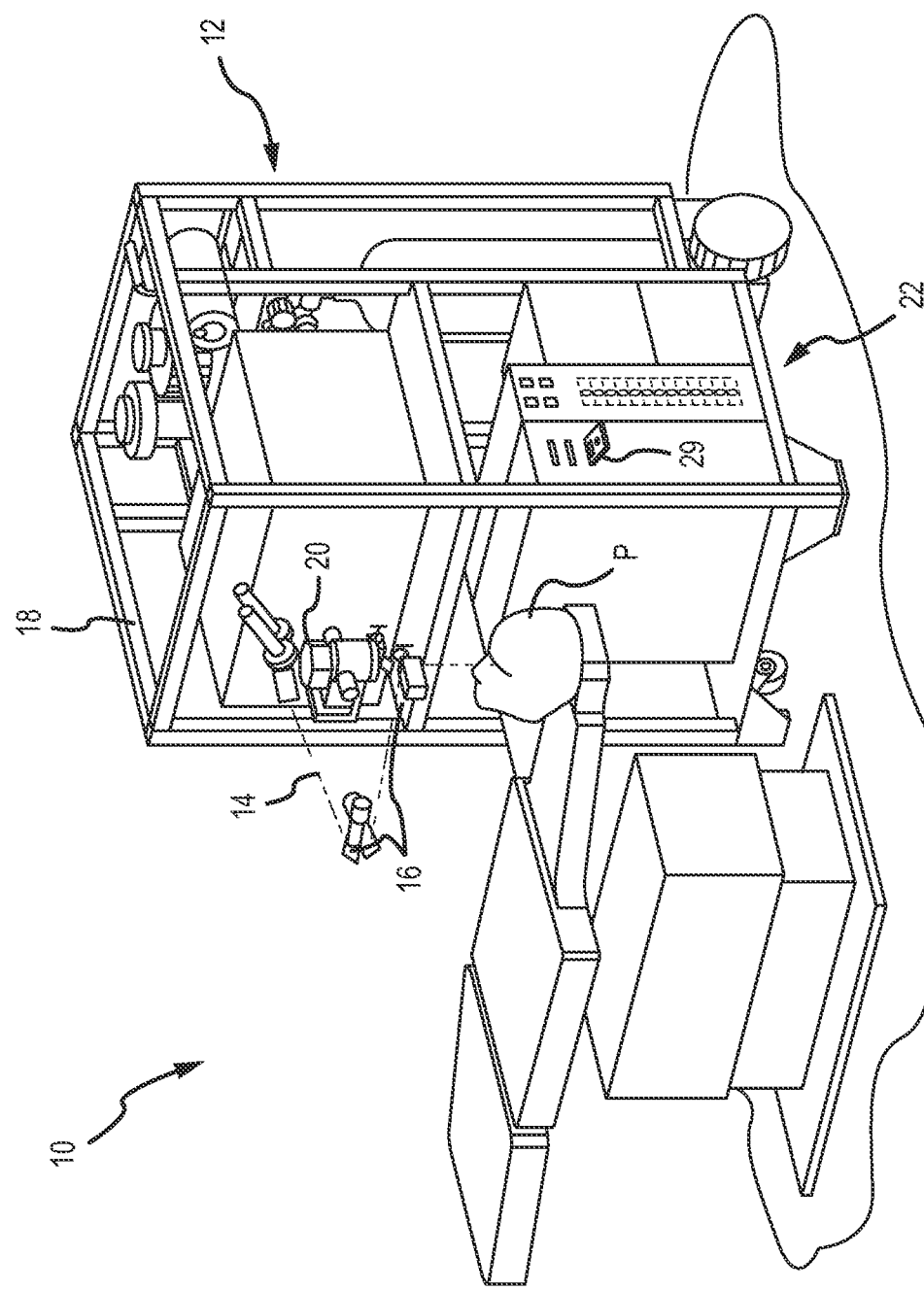
FIG. 1 illustrates a laser ablation system according to an embodiment of the present invention.

Embodiments of the present invention encompass methods and systems for ablation treatment during laser eye surgery. Treatment plans for a laser refractive surgery may benefit by taking into account a slope of the cornea surface, which affects the ablation depth of a laser pulse. A treatment plan may account for cornea surface slope by multiplying a nominal ablation depth by the cosine of the surface slope at each pulse location. The cosine may be estimated based on an ellipsoid model for the cornea surface of the patient's eye. Ellipsoid models of a patient's eye typically assume that the main axis of the ellipsoid as well as the laser beam light incident on the corneal surface are vertical. The ellipsoid model may be calculated from two curvature values and a torsional rotation angle, which may be obtained using a keratometer.

A patient's eyes may be slightly tilted in both an X direction, which corresponds to an axis intersecting both eyes, and a Y direction, which is orthogonal to the X direction. Eye tilt during laser correction surgery may correspond to the angle between the visual axis and the optical axis of the eye. When a patient fixates his or her eye on a target during a laser treatment procedure, the tilted eye may present an asymmetric surface with respect to the laser beam where the corneal surface has a steeper slope in one direction than in the opposite direction with respect to the laser beam. Embodiments of the present invention include improved cosine effect techniques, which take into account the surface slope difference or asymmetry, as well as techniques for reducing or preventing aberrations that may result from the slope difference.

Further, the asymmetric surface (e.g., cosine asymmetry) may be also affected by eye shift due to treatment misalignment. Eye shift may occur when the corneal vertex is offset from the pupil center. Eye shift as approximated by an ellipsoid model of the eye with the vertex shifted with respect to a laser beam's axis, may cause an asymmetric surface with respect to a laser beam where the corneal surface has a steeper slope in one direction than in the opposite as described above. Embodiments of the present invention also include improved cosine effect techniques which take into account these surface slope differences.

To correct for eye tilt and/or eye shift, a cosine adjustment coefficient can be calculated and applied to an ablation treatment plan. The cosine adjustment coefficient may be calculated by constructing a model that approximates the corneal surface of the patient's eye and that accounts for eye tilt and/or eye shift. The corneal slopes of the model can be calculated and adjusted according to the tilted orientation of the corneal surface model to obtain the cosine adjustment coefficient. An ideal or target ablation may be modified based on the cosine adjustment coefficient to account for eye tilt and/or eye shift. The ablation energy and/or pulse duration of the laser beam may be varied based on the modified ablation treatment.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
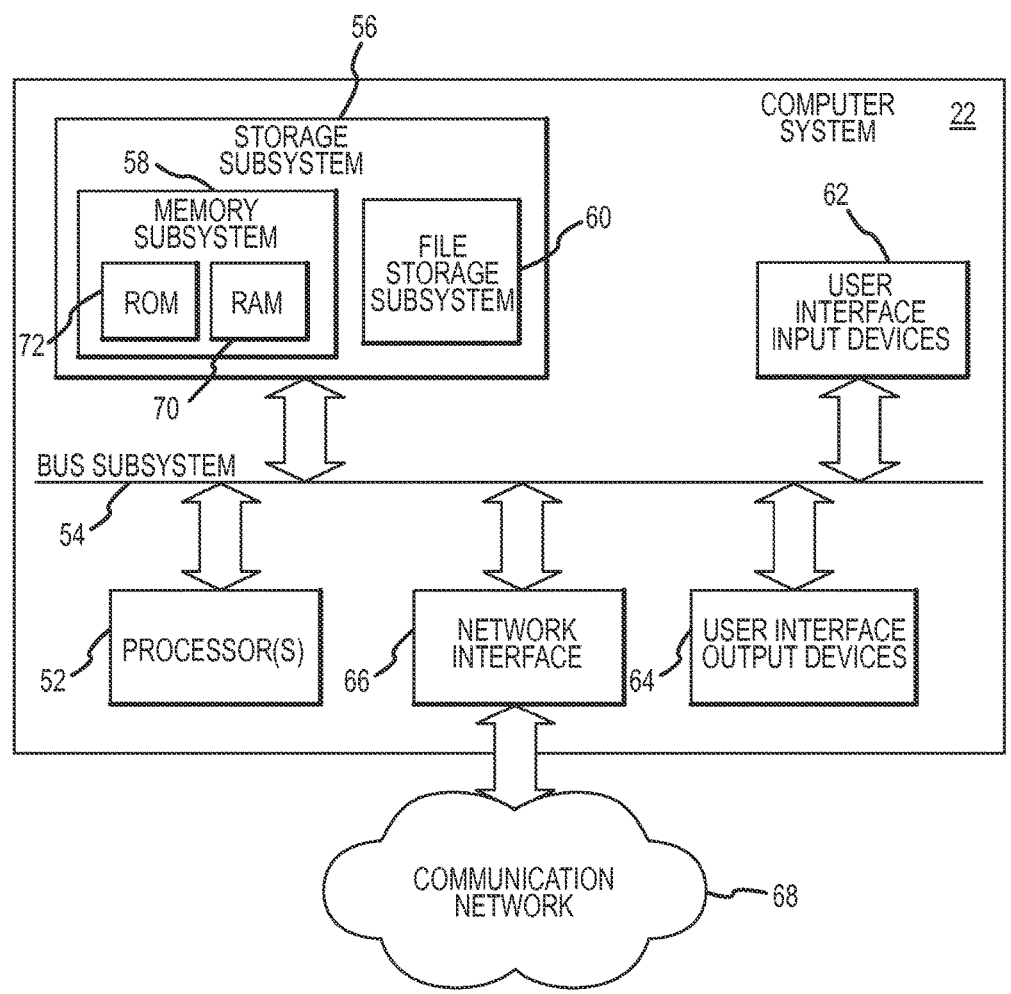
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
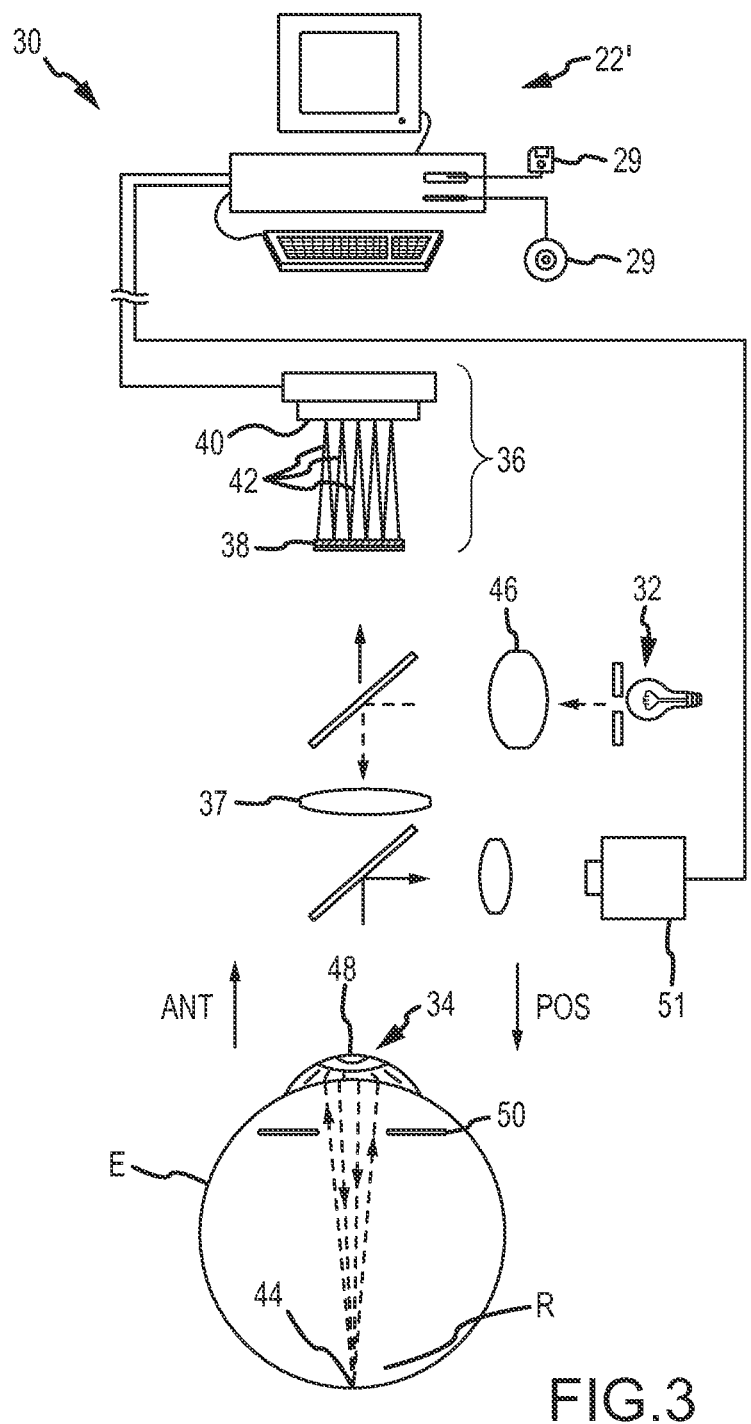
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
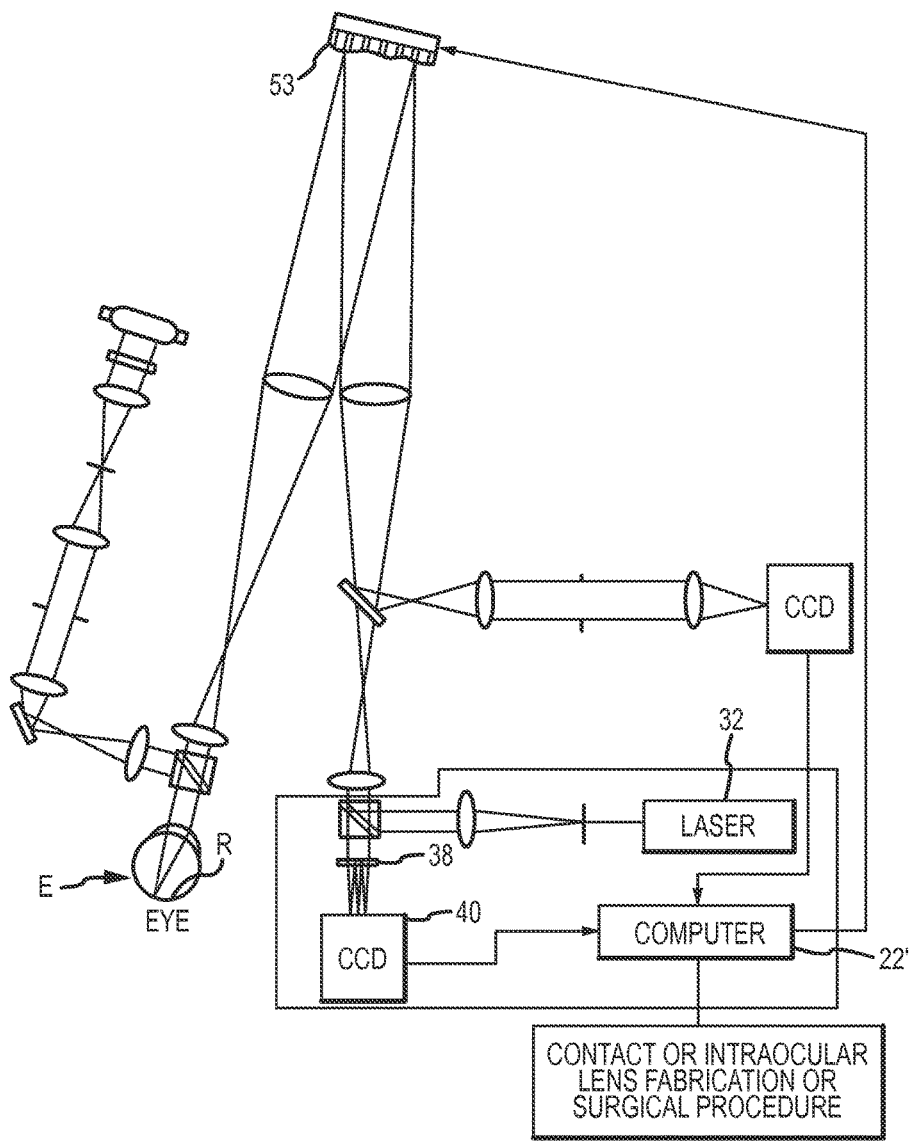
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from Abbott Medical Optics Inc., Santa Ana, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by AMO WaveFront Sciences, LLC, including the COAS wavefront aberrometer, the ClearWave contact lens aberrometer, the CrystalWave IOL aberrometer, and the like.

Tilt Induced Asymmetry and Aberrations

Figure 4A:
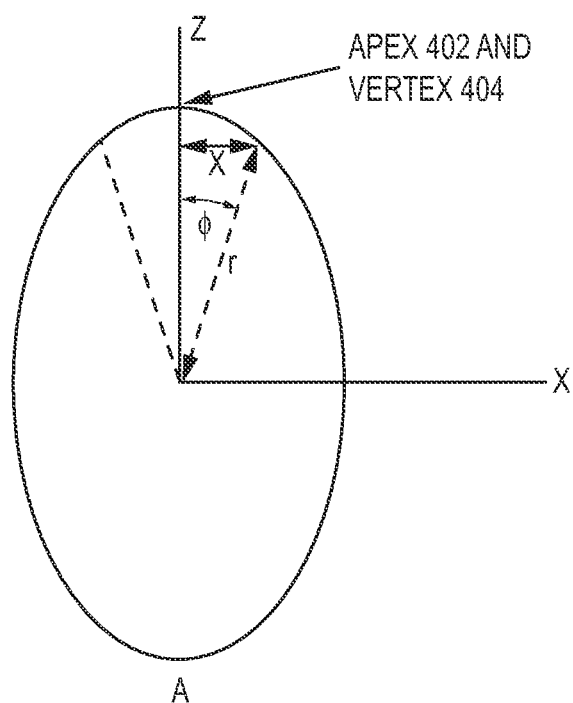
FIG. 4A illustrates a two dimensional elliptical approximation of the profile of an eye according to an embodiment of the present invention.

Referring now to FIG. 4A, illustrated is a two dimensional approximation of an eye's surface in the Z-X plane. The eye's surface is approximated as an ellipse 400, although the approximation could include other shapes, such as a biconic. The major axis 401 of the ellipse is aligned with the Z axis so that the corneal vertex 404 of the approximated eye (e.g., the point on the upper portion of the ellipse where the tangent is parallel to the x axis) is equivalent to the apex 402 of the ellipse (e.g., the point where the major axis 401 intersects the upper portion of the ellipse). In such a configuration, the Z axis axially aligns with the optical axis of the eye. The approximated eye ellipsoid shape may be calculated from two curvature values of a patient's eye and the torsional rotation angle of the ellipsoid. The curvature values and/or torsional rotation angle may be obtained by a keratometer.

Figure 4B:
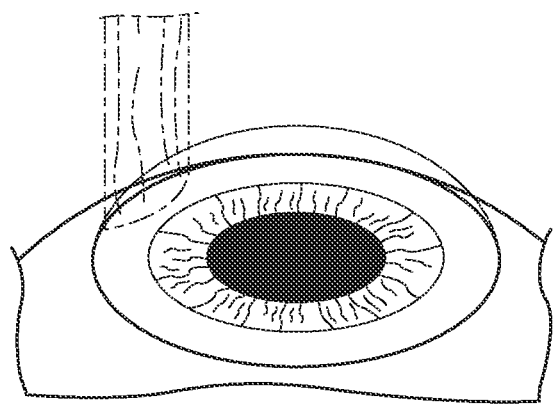
FIGS. 4B-C illustrate various effects the sloped corneal surface of an eye may have on a laser ablation treatment according to an embodiment of the present invention.
Figure 4C:
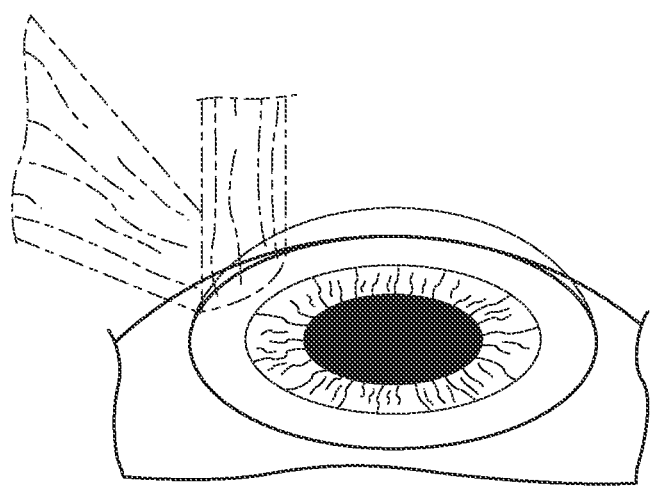

In laser ablation treatments the laser beam is typically axially aligned with the Z axis. Due to the sloped contour of the cornea surface, ablations of the cornea experience a cosine effect as the ablations move radially outward from the Z axis. As shown in FIG. 4B, as the laser beam moves to the peripheral cornea a distance X from the Z axis, the laser beam incident upon the corneal surface of the eye experiences ovalization due to the curved surface of the cornea. Likewise, as shown in FIG. 4C, a portion of the laser beam is reflected from the peripheral cornea surface due to the lack of perpendicular energy being delivered to the cornea. The laser beam energy is attenuated at the peripheral cornea due to ovalization and reflection, which affects the ablation depth per a laser pulse. Steeper corneal slope profiles may result in larger cosine effects compared to gradual corneal slope profiles. To account for the cosine effect, a laser ablation treatment may employ a cosine adjustment measure, which may include multiplying a nominal ablation depth by the cosine of the surface slope at each pulse location. For example, the intensity of the laser beam energy and/or the duration of the laser treatment at the peripheral corneal portions may be increased to compensate for the cosine effect of the measured corneal surface profile. An example of such an ablation treatment procedure is provided in commonly assigned U.S. Pat. No. 7,419,485, the full disclosure of which is incorporated herein by reference.

Figure 5A:
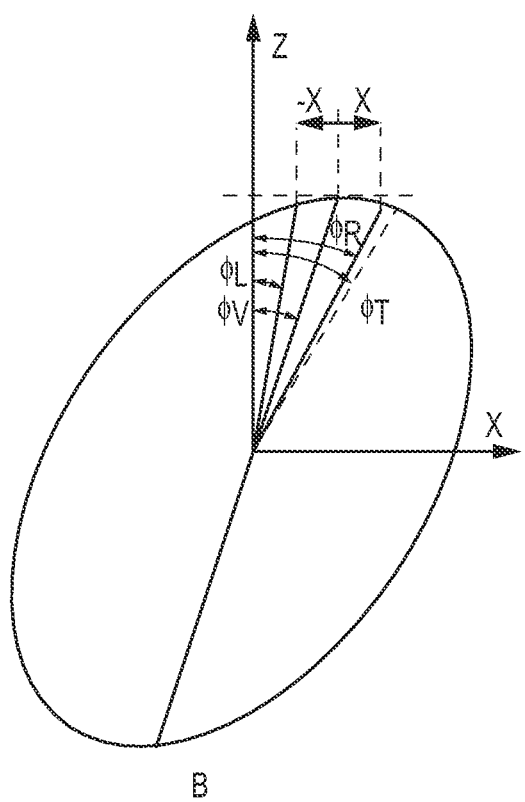
FIG. 5A illustrates a two dimensional elliptical approximation of a tilted profile of an eye according to an embodiment of the present invention.

In some instances the patient's eye may be slightly tilted in relation to the axis of the laser beam. FIG. 5A, illustrates an approximation of a tilted profile for an eye surface in the Z-X plane. As in FIG. 4A, the Z axis typically corresponds to the axis of the laser beam. In the tilted orientation, the approximated corneal vertex of the eye 502 is offset from the apex 504 and/or the Z axis. The tilted orientation results in an asymmetric corneal surface relative to the corneal vertex 502 where the corneal surface has a different surface slope in one direction measured from the corneal vertex (plus X direction of FIG. 5A) than in the opposite direction (minus X direction of FIG. 5A). The result is generally that the surface slope is steeper in one direction than in the opposite direction. The tilted orientation produces an asymmetric cosine effect at opposite peripheral corneal edges. Embodiments of the present invention provide treatment systems and methods which take into account the asymmetry as well as any alignment variations between the laser treatment device and the patient's eye. For example, the treatment target, which is aligned with the pupil center, may be offset from the corneal vertex of the approximated patient's eye. This may also produce an asymmetric cosine effect at opposite peripheral corneal edges.

Although FIG. 5A illustrates a tilted orientation of an ellipsoid approximation of the eye in the Z-X plane, the patient's eye may have a similar tilted orientation in the Z-Y plane. The tilted orientation of a patient's eye may correspond to the angle between the visual axis 512 (i.e., the axis from the center of the pupil to the fovea 510) and optical axis 506 (i.e., the axis through the center of the cornea and the apex 504). In the tilted orientation, the optical axis 506 of the patient's eye is typically angularly offset from the axis of the laser beam. The tilted orientation of the patient's eye may be apparent as the patient fixates his or her eye on a target on during a laser ablation treatment.

Figure 5B:
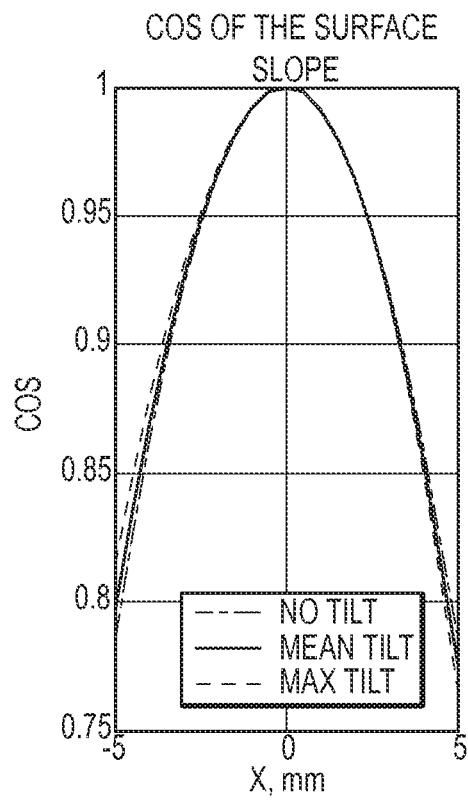
FIGS. 5B-C provide graphical illustrations of a cosine effect asymmetry that may result due to a tilted orientation of an eye according to an embodiment of the present invention.
Figure 5C:
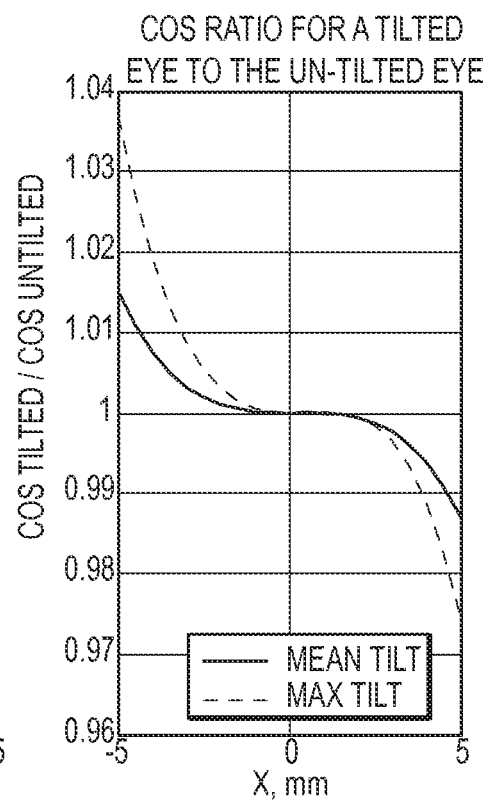
Figures 5D, 5E:
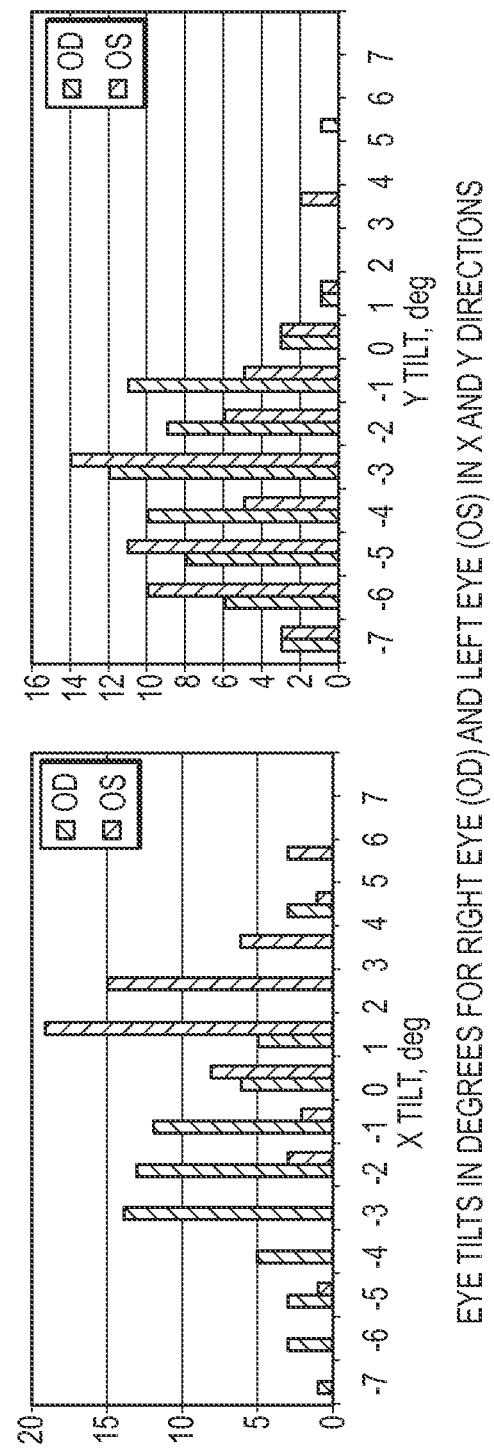
FIGS. 5D-E provide histograms of measured tilts of left and right eyes according to an embodiment of the present invention.

FIGS. 5D-E provide a histogram of measured eye tilts in degrees for patients' left and right eyes in an x direction (i.e., a direction generally parallel to an axis intersecting both eyes) and a y direction orthogonal to the x direction. The eye tilts are measured from the Z axis, which corresponds to an axis extending from a target the patient fixates on to the center of the ellipsoid approximation. FIGS. 5D-E illustrate that the right eye (OD) is generally negatively rotated from the Z axis while the left eye (OS) is generally positively rotated from the Z axis. The result is that the visual axis of both eyes is typically on the nasal side of the optical axis. FIGS. 5D-E also illustrate that the tilt for both right and left eyes are negative in the y direction, resulting in both eyes typically pointing slightly vertically downward.

The mean tilt and standard deviation for the left and right eyes in the x direction is provided in table 1 below. As illustrated, the mean values for horizontal tilts (x direction) are approximately half the typical value reported for the angle (i.e., 5 deg) between the eye's visual axis and optical axis.

TABLE 1

Horizontal eye tilt statistics for left and right eyes

| | OD | | OS | |
|---|---|---|---|---|
| Tx | mean | std | mean | std |
| deg | −1.7 | 2.7 | 2.3 | 2.9 |

Using the formulas provided below, the cosine effect asymmetry of the eye's tilted orientation may be calculated.

a. Equations for an Ellipsoid with No Tilt

The equation for an ellipsoid with no tilt is:

$$\frac{x^2}{a^2} + \frac{y^2}{b^2} + \frac{z^2}{c^2} = 1 \tag{A1}$$

To find the surface slope of an non-tilted ellipsoid at any point (x, y) on the ellipsoid surface, the following equations may be used:

A general quadric surface can be described by:

$$P(1) \cdot x^2 + P(2) \cdot y^2 + P(3) \cdot z^2 +$$

$$P(4) \cdot xy + P(5) \cdot xz + P(6) \cdot yz +$$

$$P(7) \cdot x + P(8) \cdot y + P(9) \cdot z = 1 \tag{B1}$$

For a given point on the surface with coordinates x,y, the height of the surface at this point is:

$$z = \frac{-B + \sqrt{B^2 - 4 \cdot P(3) \cdot C}}{2P(3)} \tag{B2}$$

B and C are defined by the following equations:

$$B = P(5) \cdot x + P(6) \cdot y + P(9)$$

$$C = P(1) \cdot x^2 + P(2) \cdot y^2 + P(4) \cdot xy + P(7) \cdot x + P(8) \cdot y - 1 \tag{B3}$$

From (B1) we can find the differential form:

$$P(1) \cdot x \cdot dx + P(2) \cdot y \cdot dy + P(3) \cdot z \cdot dz + P(4) \cdot x \cdot dy + P(4) \cdot dx \cdot y +$$

$$P(5) \cdot x \cdot dz + P(5) \cdot dx \cdot z + P(6) \cdot y \cdot dz + P(6) \cdot dy \cdot z +$$

$$P(7) \cdot dx + P(8) \cdot dy + P(9) \cdot dz = 1 \tag{B4}$$

This gives us the surface gradient components:

$$\frac{\partial z}{\partial x} = -\frac{P(1) \cdot x + P(4) \cdot y + P(5) \cdot z + P(7)}{P(3) \cdot z + P(5) \cdot x + P(6) \cdot y + P(9)} \tag{B5}$$

$$\frac{\partial z}{\partial y} = -\frac{P(2) \cdot y + P(4) \cdot x + P(6) \cdot z + P(8)}{P(3) \cdot z + P(5) \cdot x + P(6) \cdot y + P(9)}$$

The slope of the non-tilted surface ($\nabla z$) is:

$$|\nabla z| = \sqrt{\left(\frac{\partial z}{\partial x}\right)^2 + \left(\frac{\partial z}{\partial y}\right)^2} \tag{B6}$$

$$= \sqrt{\frac{(P(1) \cdot x + P(4) \cdot y + P(5) \cdot z + P(7))^2 +}{(P(2) \cdot y + P(4) \cdot x + P(6) \cdot z + P(6))}{(P(3) \cdot z + P(5) \cdot x + P(6) \cdot y + P(9))}}$$

b. Equations for an Ellipsoid Tilted in the X Direction

Referring to FIG. 5A, the following notations are used in the equations below:

φ—angle of a radius to a point on the ellipse, relative to the vertical axis Z;

$\phi_T$—angle of the ellipse tilt, i.e. angle of the ellipse apex relative to the vertical axis;

$\phi_V$—angle of the ellipse vertex, where the ellipse surface is horizontal;

$\phi_R$—angle of the ellipse point, located at the distance +X from the vertex;

φL—angle of the ellipse point, located at the distance −X from the vertex;

α—angle of the ellipse surface slope;

$\alpha_R$—angle of the ellipse surface slope at the distance +X from the vertex;

$\alpha_L$—angle of the ellipse surface slope at the distance −X from the vertex.

For a non-tilted ellipse the angle ϕ of the point at the distance X from the ellipse apex 402 (see FIG. 4A—for a non-tilted ellipse, the apex is the same as the vertex) is:

$$\tan\phi = \frac{X/c}{\sqrt{1-(X/a)^2}} \qquad (A2)$$

The slope of a non-tilted ellipse at the distance X from the apex is:

$$\tan\alpha = \left(\frac{c}{a}\right)^2 \frac{X/c}{\sqrt{1-(x/a)^2}} = \left(\frac{c}{a}\right)^2 \tan\phi \qquad (A3)$$

From the equation for an ellipse (A1 above) with y=0, the radius (r) from the center of the ellipse at the angle ϕ is:

$$r = \left(\frac{\cos^2\phi}{c^2} + \frac{\sin^2\phi}{a^2}\right)^{-1/2} \qquad (A4)$$

From the equation A3, the slope as a function of the angle ϕ relative to the vertical axis can be determined:

$$\tan(\alpha - \phi_T) = \left(\frac{c}{a}\right)^2 \tan(\phi - \phi_T) \qquad (A5)$$

Since the vertex is defined as a point with zero slope in the tilted orientation (i.e., the topmost point on the ellipse), the angle $\phi_V$ of the vertex may be determined by the following equation:

$$\tan(-\phi_T) = \left(\frac{c}{a}\right)^2 \tan(\phi_V - \phi_T) \qquad (A6)$$

This provides the following equation for $\phi_V$:

$$\phi_V = \phi_T - \operatorname{atan}\left(\left(\frac{a}{c}\right)^2 \tan\phi_T\right) \qquad (A7)$$

Using equation A4, the ellipse radius at the angle ϕ can be derived from the following equation:

$$r(\phi) = \left(\frac{\cos^2(\phi-\phi_T)}{c^2} + \frac{\sin^2(\phi-\phi_T)}{a^2}\right)^{-1/2} \qquad (A8)$$

The angle ϕ of a point at the distance X from the ellipse vertex can be determined using the function in A8 by solving the following equation:

$$X = r(\phi)\cdot\sin(\phi) - r(\phi_V)\cdot\sin(\phi_V) \qquad (A9)$$

Once the angle ϕ(X) for a point is determined, the surface slope at this point can be calculated using the formula in A5:

$$\alpha = \operatorname{atan}\left[\left(\frac{c}{a}\right)^2 \tan(\phi(X) - \phi_T)\right] + \phi_T \qquad (A10)$$

c. Equations for an Ellipsoid Tilted in the X and Y Directions

The surface slope of the entire 2D surface of the ellipsoid tilted in both the X and Y directions can be determined by transforming equation A1 for a tilted ellipsoid as follows:

$$\frac{(x\cos(\phi_T) - z\sin(\phi_T))^2}{a^2} + \frac{y^2}{b^2} + \frac{(x\sin(\phi_T) + z\cos(\phi_T))^2}{c^2} = 1 \qquad (A11)$$

From this equation the differential form is determined as:

$$\frac{(x\cos(\phi_T) - z\sin(\phi_T))}{a^2}dx + \frac{y}{b^2}dy + \frac{(x\sin(\phi_T) + z\cos(\phi_T))}{c^2}dz = 0 \qquad (A12)$$

This provides an equation for the surface slope ($\nabla z(\phi_T)$) of the tilted ellipsoid:

$$|\nabla z(\phi_T)| = \sqrt{\left(\frac{\partial z}{\partial x}\right)^2 + \left(\frac{\partial z}{\partial y}\right)^2} \qquad (A13)$$

$$= \sqrt{\left(\frac{x'\cos(\phi_T)/a^2 + z'\sin(\phi_T)/c^2}{x'\sin(\phi_T)/a^2 - z'\cos(\phi_T)/c^2}\right)^2 + \left(\frac{y/b^2}{x'\sin(\phi_T)/a^2 - z'\cos(\phi_T)/c^2}\right)^2}$$

FIGS. 5B-C provide graphical illustrations of the cosine effect asymmetry in the X-Z plane due to the tilted orientation of a patient's eye. Specifically, FIG. 5B illustrates the cosine of the surface slope of a patient's eye in the x direction for an un-tilted eye, a mean eye tilt of 5 degrees, and a maximum eye tilt of 11 degrees of an eye approximated having a major axis of 11.7 mm (i.e., c=11.7 mm) and a minor axis of 9.4 mm (i.e., a=9.4 mm). The surface slope cosines were calculated to a distance of approximately 5 mm on both sides of the corneal vertex (see FIG. 5A).

As illustrated in FIG. 5B, an un-tilted eye has a symmetrical surface slope cosine profile with a cosine of approximately 0.78 at 5 mm on either side of the corneal vertex. With a tilt of 5 degrees, the cosine asymmetry is such that the cosine value at −5 mm from the corneal vertex is approximately 0.80 and the cosine value at +5 mm from the corneal vertex is approximately 0.76. A tilt of 11 degrees produces a more drastic asymmetry with a cosine value of approximately 0.83 at −5 mm and a cosine value of approximately 0.73 at +5 mm. Similarly, FIG. 5C illustrates the ratio of the cosine value of a mean tilt of 5 degrees and the cosine value of a max tilt of 11 degrees versus the cosine value of an un-tilted eye. FIG. 5C illustrates that the cosine values increasingly deviate from symmetry (about the corneal vertex) as the tilt orientation increases. While FIGS. 5A-C focus on a tilted corneal surface in the X-Z plane, these figures and the accompanying description are merely illustrative of the cosine asymmetry due to the tilted orientation and it should be realized that such asymmetry may occur in any plane of the ellipsoid. As described in the equations above, the surface slope of the entire 2D surface of the tilted ellipsoid can be determined so that the cosine asymmetry of the patient's entire corneal surface is known.

The cosine asymmetry due to the tilted orientation may result in the formation of ablation treatment induced aberrations. For example, the cosine asymmetry may deviate the actual ablation of corneal tissue from the target or ideal ablation treatment, which may cause high-order aberrations to appear, such as spherical aberrations or Coma. Given the ablation refraction and the characteristics of the corneal profile of the eye, the high order aberrations that may be induced from the cosine asymmetry may be estimated as provided below in the examples section.

Using the surface slope values of the ellipsoid surface (either non-tilted, tilted, or both), the cosine values may be calculated and a cosine adjustment measure determined for one or more points (x, y) on the ellipsoid surface. Using the cosine adjustment measure, an ablation treatment may be modified or adjusted to account for the tilt of the patient's eye. This may reduce or substantially eliminate the formation of ablation treatment induced aberrations. For example, using the surface slopes of the ellipsoid surface (both the non-tilted surface slopes and the tilted surface slopes above), an adjustment coefficient, $C_{asym}$, may be obtained for the entire corneal surface of the eye from the following equation:

$$C_{asym} = |\nabla z(\phi_T)|/|\nabla z(0)|$$

The equations for $\nabla z(\phi_T)$ and $\nabla z(0)$ are provided and described above. See e.g., equations (A13) and (B6) respectively. Using the adjustment coefficient, $C_{asym}$, a target or ideal ablation treatment $A_0$ may be modified or adjusted to account for tilt by multiplying the ideal ablation treatment by the adjustment coefficient: $A_0 * C_{asym}$. In this manner an ablation treatment may account for the cosine asymmetry of the eye due to tilt and thereby reduce or eliminate the formation of ablation induced aberrations.

In some embodiments it may be desirous to include or retain a certain amount of induced high order aberrations, such as to increase depth of focus. In such embodiments the amount of induced high order aberrations may be controlled rather than eliminated. As such, the equations described herein may be used and/or modified to control induced high order aberrations rather than eliminate such aberrations.

Figure 6A:
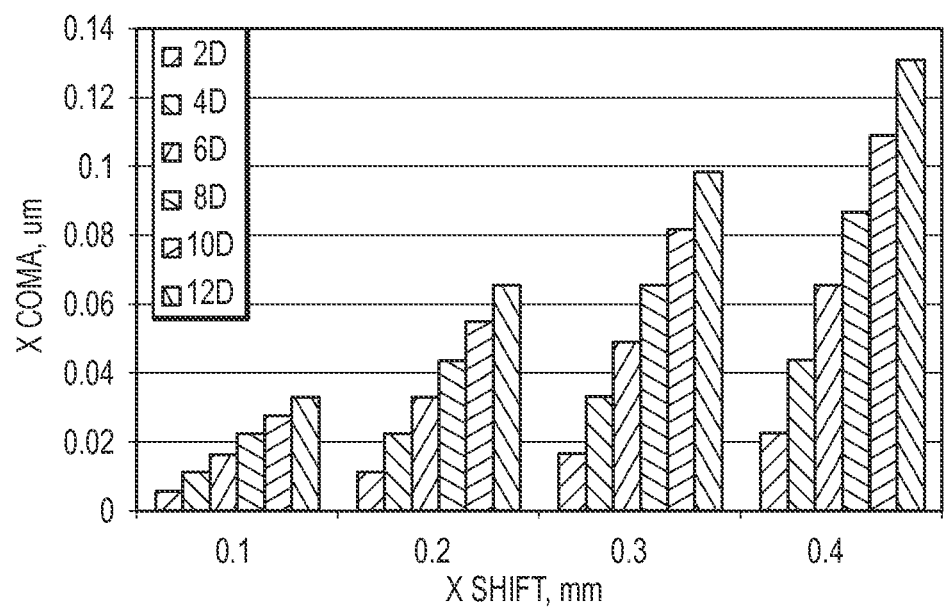
FIG. 6A provides a graphical illustration of effects that de-centering may have during a laser ablation treatment according to an embodiment of the present invention.
Figure 6B:
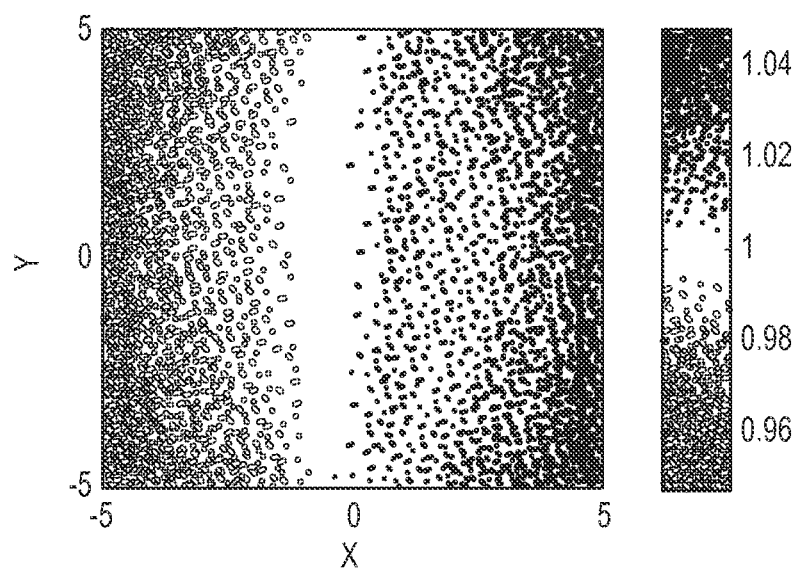
FIG. 6B provides a graphical illustration of an adjustment coefficient for a de-centering shift according to an embodiment of the present invention.

As mentioned above, cosine asymmetry may also be caused or further enhanced by de-centering of the treatment device. De-centering may occur when the laser beam is not aligned with the corneal vertex of the tilted eye. Asymmetry due to de-centering may result in the formation of ablation induced high-order aberrations, such as spherical aberrations, Coma, and the like. FIG. 6A illustrates estimated coma inducement due to de-centering for various diopters and various de-centering shifts. The estimates were calculated from an ellipsoid model with the following parameters: a=9.2 mm, b=9.2 mm, and c=11.2 mm. With a magnitude of de-centering, 0.3 mm, the shift-induced coma may reach 0.1 um for high-myopia treatments (e.g., 8-10D). FIG. 6B illustrates a cosine asymmetry adjustment coefficient for an 8 diopter myopia eye having a 0.3 mm de-centering shift in the X direction. The equations presented above may be modified to account for de-centering of the laser ablation treatment. The modifications can be done by shifting X and Y coordinates as follows:

$$X' = X + \Delta X\text{pupil}$$

$$Y' = Y + \Delta Y\text{pupil}$$

Here X' and Y' are the new coordinates, which should be used in place of X and Y in the formulas above. $\Delta X$pupil and $\Delta Y$pupil are the shifts of the pupil center relative to the vertex.

Ablation Treatments Based on Tilted Orientation

Figure 7:
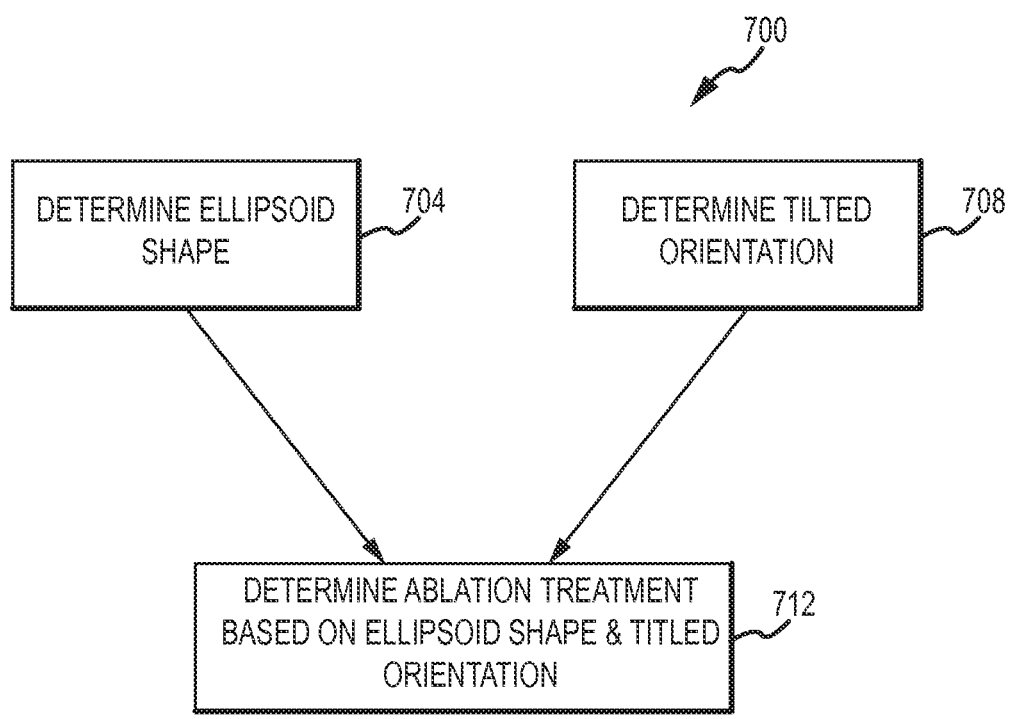
FIG. 7 illustrates a method for determining an ablation treatment based on a tilted orientation according to an embodiment of the present invention.

Referring to FIG. 7, illustrated is a flow diagram 700 of a method for determining an ablation treatment based on a tilted orientation of a patient's eye. In some cases, the determination may involve modifying or adjusting an ablation treatment to account for cosine asymmetry due to the tilted orientation. At block 704, an ellipsoid shape may be determined that approximates the corneal surface of the patient's eye. The parameters for the ellipsoid shape may be determined through a variety of factors. For example, a keratometry measurement may be performed to obtain the curvature value of the steepest meridian of the patient's eye (k1 value), the curvature value of the meridian orthogonal to the steepest meridian (k2 value), and the torsional rotation angle (k2A value). These three parameters may be used to construct a corneal ellipsoid that approximates the patient's eye. Alternatively or additionally, a corneal topography elevation map H(x, y) may be measured and/or obtained for the corneal surface of the patient's eye, from which an ellipsoid model may be constructed.

According to another embodiment, population averages may be obtained for corneal ellipsoid shapes and a corneal ellipsoid may be constructed from the population average values to approximate the corneal surface of the patient's eye. Further, another model shape may be constructed to approximate the patient's eye, such as a biconic or other shape. The biconic shape and/or other model shape may be based on topography measurements, keratometry measurements, and/or population average measurements.

At block 708, the tilted orientation of the ellipsoid shape (or other shape) may be determined. For example, according to one embodiment, a corneal topography elevation map H(x, y) may be fitted onto the model ellipsoid shape to determine the tilted orientation. A Linear least-square fit, or any other optimization technique, can be used to adjust the ellipsoid model parameters until the model shape best fits the topography data. Examples of least-square fit techniques are generally described in "Solving Least Square Problems," L. L. Lawson, R. J. Hanson, Prentice-Hall, Inc., Englewood Cliffs, N.J., 1974, which is incorporated by reference herein. Fitting the topography data onto the model ellipsoid or other shape yields the model shape parameters. For an ellipsoid, these model shape parameters include the axes sizes (i.e., a, b, & c of equation A1), the apex position, and the like. Alternatively or additionally, population averages may be obtained for the tilted orientation of patients' eyes and a tilted corneal ellipsoid may be constructed from the population average values to approximate the tilted orientation of the corneal surface of the patient's eye.

The measured and/or calculated model ellipsoid parameters for the patient's eye may be compared against the population averages and a warning may be produced if the patient's model ellipsoid parameters appear beyond a predefined population average criteria (e.g., beyond 3 times the standard deviation). Similarly, an offset of the corneal vertex relative to the pupil center may be obtained and/or determined. This offset value may be used with the model parameters to determine a model surface (i.e., ellipsoid) that approximates the patient's eye.

At block 712, an ablation treatment for the patient may be determined based on the ellipsoid shape and the tilted orientation. For example, the corneal surface slopes (i.e., non-tilted, tilted, or both) in the ablation area may be calculated and a cosine adjustment coefficient, $C_{asym}$, may be determined and applied to an ideal or target ablation $A_0$. From the model shape parameters, the equations above may be used to determine the surface slopes of the ellipsoid and the adjustment coefficient, $C_{asym}$, may be determined.

In some embodiments, treatment plans or shapes based on the measured topography and/or keratometry data may be adjusted or further defined based on measured patient wavefront data. For example, after the cosine adjustment coefficient, $C_{asym}$, is applied to the ideal or target ablation $A_O$, wavefront data may be used to further adjust the ablation treatment plan. In other embodiments, wavefront data may be used in combination with application of the cosine adjustment coefficient, $C_{asym}$, to the ideal or target ablation $A_O$ to determine or optimize the adjusted ablation treatment plan.

Figure 8:
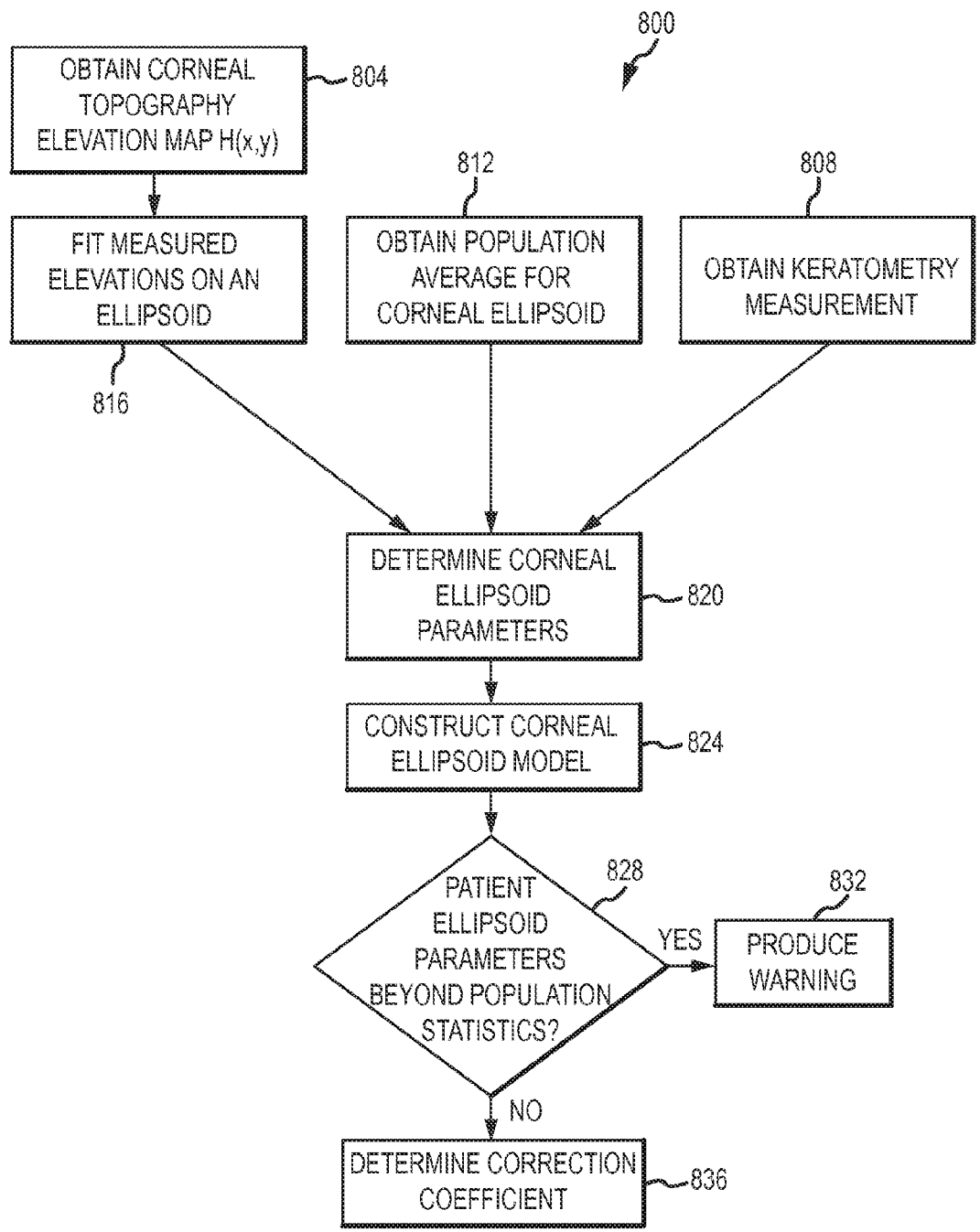
FIG. 8 illustrates another method for determining an ablation treatment based on a tilted orientation according to an embodiment of the present invention.

Referring now to FIG. 8, illustrated is another flow diagram 800 of a method for determining an ablation treatment based on a tilted orientation according to another embodiment of the invention. At block 804, a corneal topography elevation map H(x,y) may be obtained from topography measurements of the patient's eye and/or from any other source of data (i.e., manually input by a physician). At block 816, the measured elevation may be fit onto a model shape (i.e., ellipsoid, biconic, or the like) to determine the model parameters that approximate or best approximate the patient's eye. Alternatively or additionally, at block 808, keratometry measurements (k1, k2, k2A as described elsewhere herein). The keratometry measurements may be used to determine the model shape parameters that approximate or best approximate the patient's eye. If topography or keratometry measurements are not available or in addition to using one or both of these measurements, the population average values for model corneal shapes may be obtained, such as through a database, memory, or other storage device as described herein.

At block 820, the model shape parameters (e.g., corneal ellipsoid parameters) may be determined from the topography elevation map/measurements, keratometry measurements, and/or population averages of blocks 804, 808, and 812 respectively. At block 824, a corneal shape model (i.e., ellipsoid, biconic, or the like) may be constructed from the corneal model parameters. The corneal shape model may approximate the tilted orientation of the patient's eye. Determining the tilted orientation may involve fitting the corneal topography elevation map onto the model shape and/or using population average values. At block 828, the corneal model parameters may be compared against population averages and a warning produced (block 832) if the model parameters fall outside a defined threshold. Although illustrated as occurring after block 828, block 832 determination may occur before the corneal model is constructed. If the model parameters do not fall outside the defined threshold, the cosine adjustment coefficient can be determined at block 836.

Figure 9:
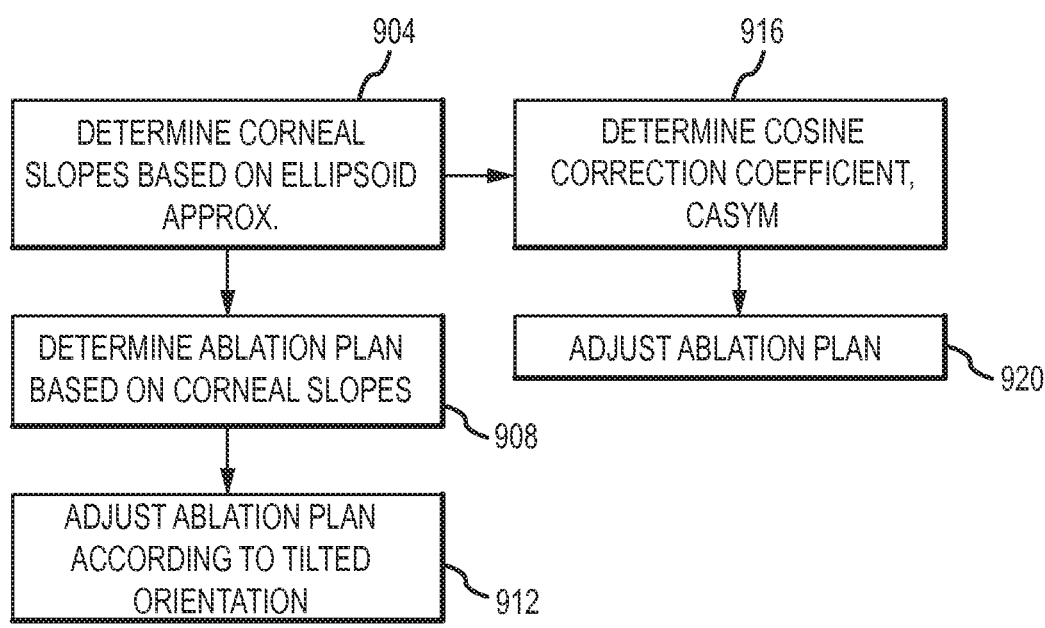
FIG. 9 illustrates another method for determining an ablation treatment based on a tilted orientation according to an embodiment of the present invention.

FIG. 9, illustrates a method for determining an ablation treatment based on the tilted orientation of the patient's eye. At block 904, the corneal slopes are determined based on the corneal surface model (e.g., corneal ellipsoid). Determining the corneal slopes may involve determining both the corneal slopes for the non-tilted corneal surface model and the corneal slopes for the tilted corneal surface model. At block 908, an ablation treatment plan is determined based on the corneal surface slopes to account for the cosine effect of the non-tilted corneal surface model. At block 912, the ablation treatment plan is adjusted according to the tilted orientation of the corneal surface model to account for the cosine asymmetry due to the tilt of the corneal surface model. Determining and/or adjusting the ablation plan in block 908 and 912 may involve calculation one or more cosine adjustment coefficients to account for the cosine values associated with the surface slopes and/or the cosine asymmetry due to the tilted orientation.

Alternatively, adjusting an ablation treatment may involve a single step or process as shown in block 916 and 920. At block 916, a cosine adjustment coefficient, $C_{asym}$, may be determined based on the surface slopes of the non-tilted and tilted corneal model ellipsoid or other shape as described herein. At block 920, an ideal or target ablation treatment may be adjusted or modified based on the cosine adjustment coefficient, $C_{asym}$. Adjusting or modifying the ablation treatment may include multiplying an ideal or target ablation treatment $A_O$ by the cosine adjustment coefficient, $C_{asym}$ (i.e., $A_O * C_{asym}$) and/or may include varying the ablation energy and/or pulse duration of the ablation laser beam. The ideal or target ablation treatment $A_O$ may be a wavefront guided or determined treatment plan.

Figure 10:
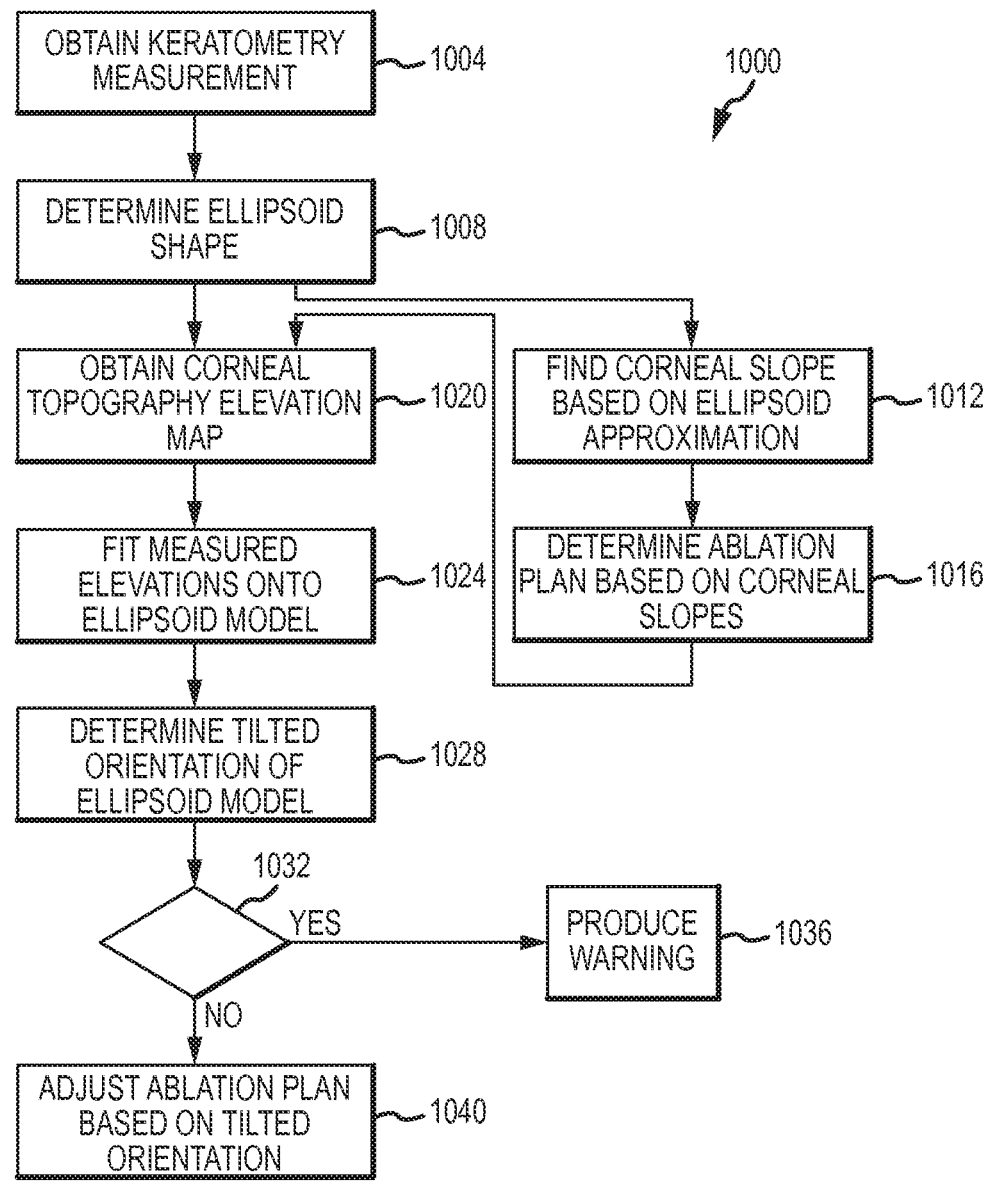
FIG. 10 illustrates another method for determining an ablation treatment based on a tilted orientation according to an embodiment of the present invention.

Referring now to FIG. 10, illustrated is a flow diagram 1000 of a method for determining an ablation treatment based on a tilted orientation that involves using both keratometry and topography measurements. At block 1004, keratometry measurements (k1, k2, k2A values) are obtained for the patient's eye. At block 1008, a corneal model ellipsoid (or other shape) is constructed based on the keratometry measurements. Following arrow "B," at block 1012, the corneal slopes of the corneal model ellipsoid are optionally calculated based on the corneal model ellipsoid, such as by using the equation (B6) described herein. The corneal slopes may be calculated for the ablation area and/or for any other defined surface of the corneal model ellipsoid.

At block 1016, an ablation treatment plan is optionally determined and/or adjusted based on the corneal slopes calculated in block 1012. Alternatively, the process may not involve the process of blocks 1012 and 1016 as shown by the arrow "A" from block 1008 to 1020. At block 1020, a corneal topography elevation map may be measured and/or obtained. At block 1024, the corneal measured elevations of the topography elevation map may be fit onto the corneal ellipsoid model using a least square fit or other optimization technique. At block 1028, the tilted orientation of the ellipsoid model may be determined, such as from the ellipsoid model parameters determined from fitting the measured topography elevations on the model ellipsoid. The tilted orientation may correspond to the orientation or position of the patient's eye as the patient fixates on a target during an ablation treatment. An offset of the corneal vertex relative to the pupil center may be obtained and used to construct the ellipsoid model (either tilted, non-tilted, or both). Further, the corneal slopes within an ablation area or other defined area may be calculated based on the tilted corneal ellipsoid model to account for cosine or other asymmetry.

At block 1032, the model ellipsoid parameters may be compared against the population average to determine whether the parameters exceed a defined threshold. If the parameters exceed the defined threshold, a warning may be produced at block 1036 to alert a physician or operator about the parameters. If the parameters do not exceed the defined threshold, an ablation treatment may be modified or adjusted based on the tilted orientation of the corneal model ellipsoid. Adjusting the ablation treatment may include adjusting the treatment determined or adjusting in block 1016 or may include adjusting an ideal or target treatment $A_O$ that is a wavefront guided or calculated ablation treatment. Adjusting the ablation treatment may also include calculating a cosine adjustment coefficient, $C_{asym}$ based on the corneal slope of the tilted and/or non-tilted corneal ellipsoid model.

Figure 11:
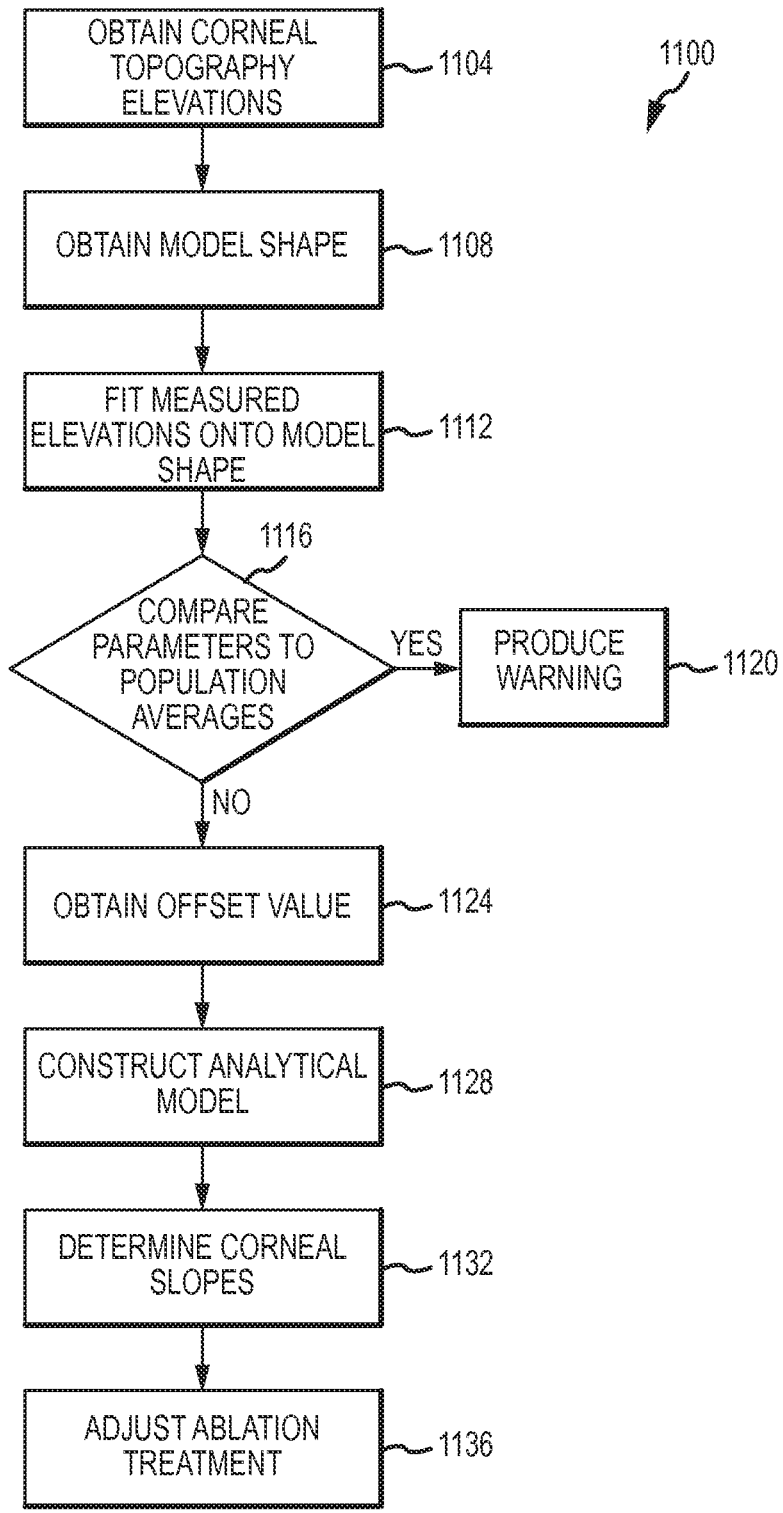
FIG. 11 illustrates another method for determining an ablation treatment based on a tilted orientation according to an embodiment of the present invention.

Referring now to FIG. 11, illustrated is a flow diagram 1100 of a method for determining an ablation treatment based on a tilted orientation using topography measurements. At block 1104, corneal topography elevations are obtained, such as by accessing a database comprising topography measurements, manually inputting the elevation, conducting a topography measurement, etc. At block 1108, a model shape is obtained, such as an ellipsoid shape, biconic shape, etc. The model shape may be constructed of population averages and/or may be constructed from the topography elevations obtained at block 1104. At block 112, the measured and/or obtained topography elevations are fit onto the model shape, such as by using an optimization technique (e.g., linear least-square). Fitting the topography elevations on the model shape yields the parameters of the model shape (e.g., axes sizes; elements a, b, c of equation A1, apex position of an ellipsoid, or the like).

At block 1116, the model shape parameters are compared against the population averages to determine if the parameters exceed a defined threshold. If the parameters exceed the defined threshold, a warning may be produced at block 1120 to warn a physician or operator. If the parameters do not exceed the defined threshold, at block 1124 an offset value may be obtained that corresponds to an offset of the corneal vertex relative to the pupil center. If this offset value is not available, the offset may be assumed to equal 0. At block 1128, an analytical corneal model may be constructed that approximates the corneal surface of the patient's eye. The analytical corneal model (e.g., the corneal ellipsoid model) may comprise a tilted orientation corresponding to the orientation of the patient's eye as the patient fixates on a target during an ablation treatment.

At block 1132, the corneal slopes of the model shape (either non-tilted, tilted, or both) may be calculated. Likewise, a cosine adjustment coefficient, $C_{asym}$, may be calculated for the corneal model shape. At block 1136, an ablation treatment may be adjusted or modified to account for the cosine asymmetry of the tilted corneal model shape. Modifying the ablation treatment may include multiplying an ideal or target ablation treatment $A_0$ by the cosine adjustment coefficient, $C_{asym}$ and/or may include varying the ablation energy and/or pulse duration of the laser beam.

Figure 13:
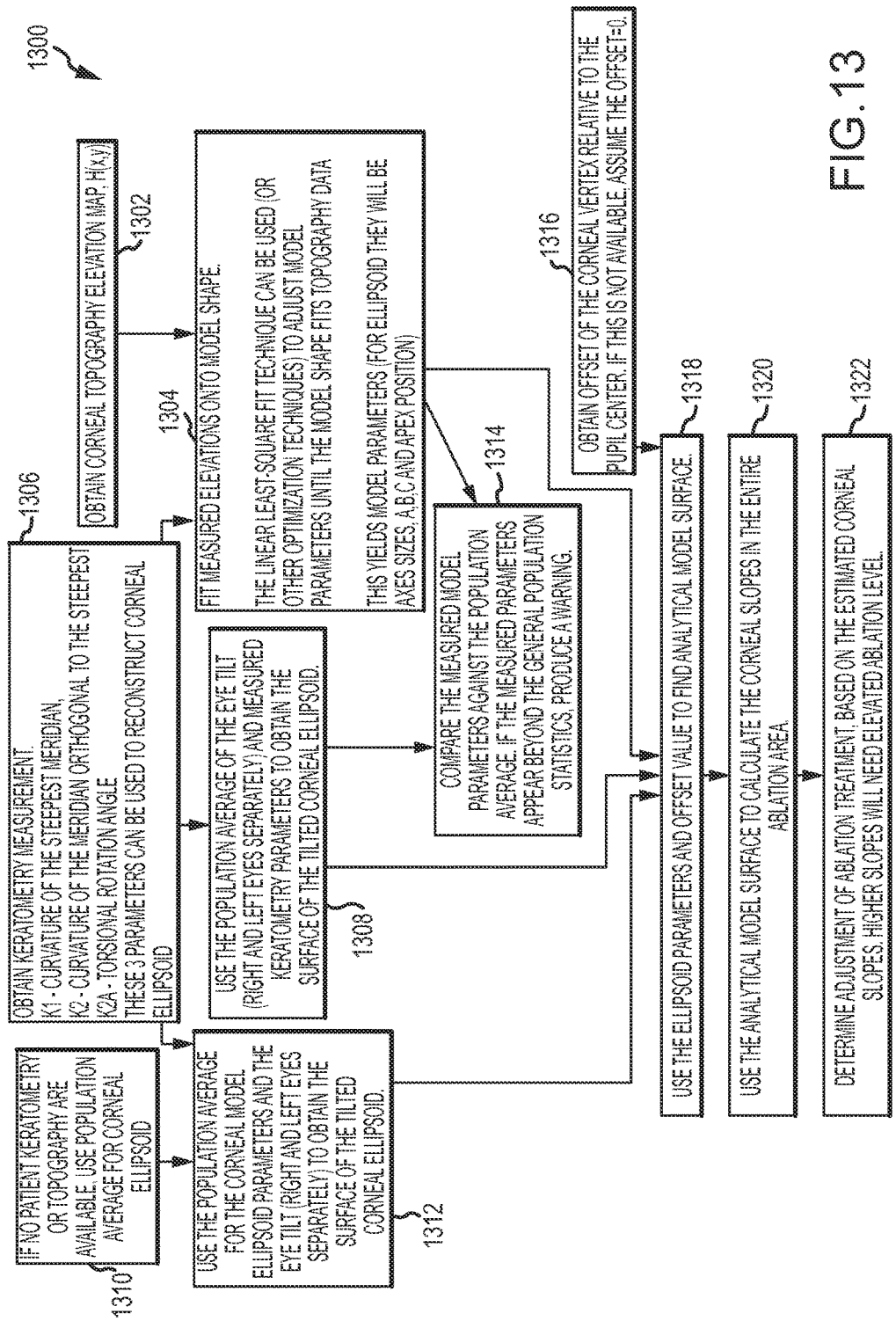
FIG. 13 illustrates another method for determining an ablation treatment based on a tilted orientation according to an embodiment of the present invention.

Referring now to FIG. 13, illustrated is another flow diagram 1300 of a method for determining an ablation treatment based on a tilted orientation according to another embodiment of the invention. At block 1302, a corneal topography elevation map H(x,y) may be obtained from topography measurements of the patient's eye and/or from any other source of data (i.e., manually input by a physician). At block 1304, the measured elevation may be fit onto a model shape (i.e., ellipsoid, biconic, or the like) to determine the model parameters that approximate or best approximate the patient's eye. A linear least square fit technique may be used (or another optimization technique) to adjust the model parameters until the model shape fits the topography data. This may yield the model parameters. For example, if an ellipsoid approximation is used this may yield the parameters for the axes sizes, such as parameters a, b, c, and apex position). Alternatively or additionally, at block 1306, keratometry measurements (k1, k2, k2A as described elsewhere herein) may be obtained for the patient's eye and/or input by a physician, where the parameter k1 may represent the curvature of the steepest meridian, k2 may represent the curvature of the meridian orthogonal to the steepest meridian, and k2A may represent the torsional rotation angle. These three parameters may be used to construct a model shape (e.g., ellipsoid shape) for the corneal ellipsoid. In some embodiments, the keratometry measurements are used in the absence of topography measurements, while in other embodiments the keratometry measurements are used with or in addition to the topography measurements. Using both measurements may provide for a check or confirmation on the accuracy of the ellipsoid approximation.

At block 1308, the population average of the eye tilts (right and left eyes) may be combined with the measured keratometry parameters to obtain an approximation of the surface of the tilted corneal ellipsoid. This may be used as an alternative or in addition to the topography measurements. At block 1314, the measured model parameters may be compared against the population averages. If the measured parameters appear beyond the general population statistics by a defined amount (e.g., greater than three standard deviations or some other amount), a warning may be produced. As an alternative to the process illustrated in blocks 1302 to 1308 or in addition to those processes, at block 1310 the population average for a corneal ellipsoid may be obtained (e.g., average curvatures, eyes tilts, and the like). The population averages may be used to obtain the corneal model parameters (e.g., ellipsoid parameters) and a model approximation of the tilted eye may be constructed from the model parameters and eye tilts.

At block 1316, the offset of the corneal vertex relative to the pupil center may be obtained. If this data is not available, the offset may be assumed to be zero. At block 1318, the model parameters (e.g., ellipsoid parameters, biconic parameters, and the like) and/or the offset value may be used to construct an analytical model of the surface of the tilted eye. At block 1320, the analytical model surface may be used to calculate the corneal slopes in the ablation area as described herein. At block 1322, an adjustment of an ablation treatment for an eye may be determined based on the estimated corneal slopes. For example, higher or greater corneal slopes may require elevated ablation levels. The described processes steps of FIG. 13 may vary. For example, FIG. 13 illustrates that block 1306 may be followed by blocks 1304 and/or 1312 so that keratometry and topography measurements are both obtained and fitted onto a model shape used a least squared or other optimization technique. Likewise, topography and/or keratometry measurements may be used with population averages to obtain model parameters and/or construct a model shape. In some embodiments, keratometry techniques, topography techniques, and population averages may all be used to obtain model parameters and/or construct a model shape. Using multiple techniques may be used to verify the model parameters and/or model shape.

Figure 14:
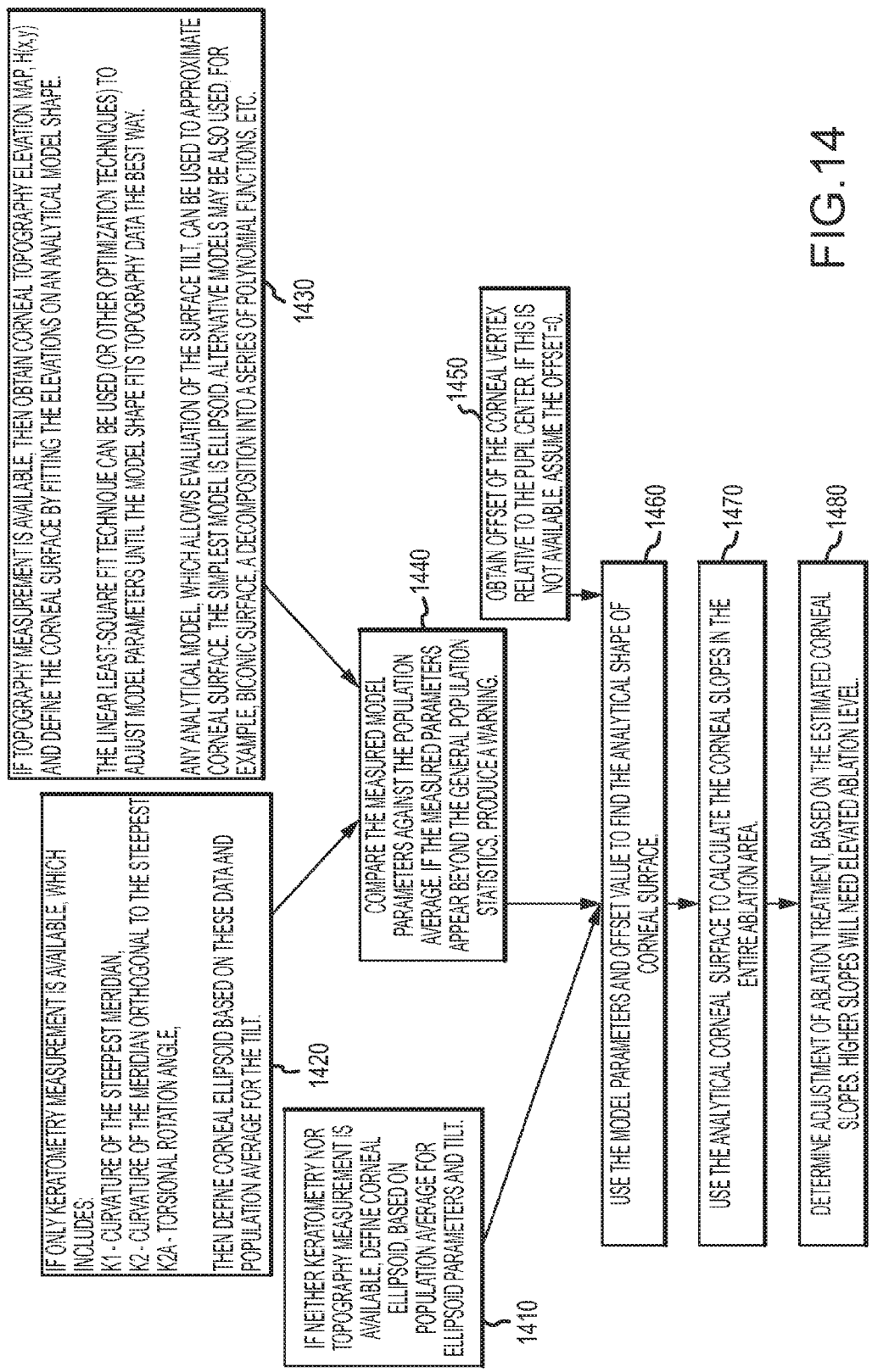
FIG. 14 illustrates another method for determining an ablation treatment based on a tilted orientation according to an embodiment of the present invention.

Referring now to FIG. 14, illustrated is another flow diagram of a method for determining an ablation treatment based on a tilted orientation of a patient's eye. At block 1430, a corneal topography elevation map H(x,y) may be obtained from topography measurements of the patient's eye and/or from any other source of data (i.e., manually input by a physician). A corneal surface of a model shape approximating the patient's eye may be defined by fitting the topography elevations on an analytical model shape. A linear least-square fit technique may be used (or any other optimization technique) to adjust model parameters until the model shape fits the topography data. Similarly, any analytical model, which allows evaluation of the surface tilt, may be used to approximate the corneal surface. For example, the simples model may be an ellipsoid. Alternative models may include a biconic surface, a cemposition into a series of polynomial functions, and the like.

Alternatively, at block 1420, keratometry measurements (k1, k2, k2A as described elsewhere herein) may be obtained for the patient's eye and/or input by a physician, where the parameter k1 may represent the curvature of the steepest meridian, k2 may represent the curvature of the meridian orthogonal to the steepest meridian, and k2A may represent the torsional rotation angle. The corneal ellipsoid may be defined based on these measurements. The tilt for the corneal ellipsoid may be determined from population tilt averages.

As an alternative to block 1420 and 1430, at block 1410, the corneal ellipsoid may be defined based on population averages for ellipsoid parameters. The tilt for the corneal ellipsoid may be determined from population tilt averages.

At block 1440, the measured model parameters may be compared against the population averages. If the measured parameters appear beyond the general population statistics by a defined amount (e.g., greater than three standard deviations or some other amount), a warning may be produced. When population averages are used to define the corneal ellipsoid and tilt, the model parameters do not need to be compared to population averages at block 1440.

Optionally, at block 1450, the offset of the corneal vertex relative to the pupil center may be obtained. If this data is not available, the offset may be assumed to be zero. At block 1460, the model parameters (e.g., ellipsoid parameters, biconic parameters, and the like) and/or the offset value may be used to construct an analytical model of the surface of the tilted eye. At block 1470, the analytical model surface may be used to calculate the corneal slopes in the entire ablation area as described herein. At block 1480, an adjustment of an ablation treatment for an eye may be determined based on the estimated corneal slopes. For example, higher or greater corneal slopes may require elevated ablation levels.

Figure 15:
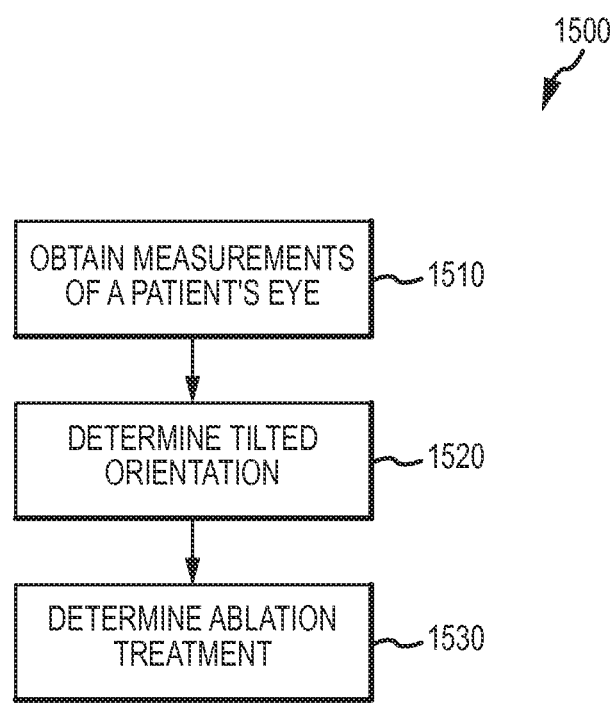
FIG. 15 illustrates another method for determining an ablation treatment based on a tilted orientation according to an embodiment of the present invention.

Referring to FIG. 15, illustrated is a flow diagram 1500 of a method for determining an ablation treatment based on a tilted orientation of a patient's eye. In this method, the ablation treatment is determined directly from the measurements of a patient's eye. In other words, the ablation treatment is determined without having to adjust a pre-existing ablation treatment or target ablation $A_0$. At block 1510, measurements of a patient's eye are obtained. Obtaining measurements of the patient's eye may involve topography and/or keratometry measurements as described herein. At block 1520, a tilted orientation of the patient's eye is determined. Determining the tilted orientation of the patient's eye may involve constructing an ellipsoid model shape (or other model shape) from the measurements of the patient's eye as described herein. At block 1530, an ablation treatment for the patient may be determined based on the tilted orientation. The ablation treatment may be determined directly from the measurements of the patient's eye and/or directly from the tilted orientation without adjusting an ideal or target ablation $A_0$.

EXAMPLES

Figure 12A:
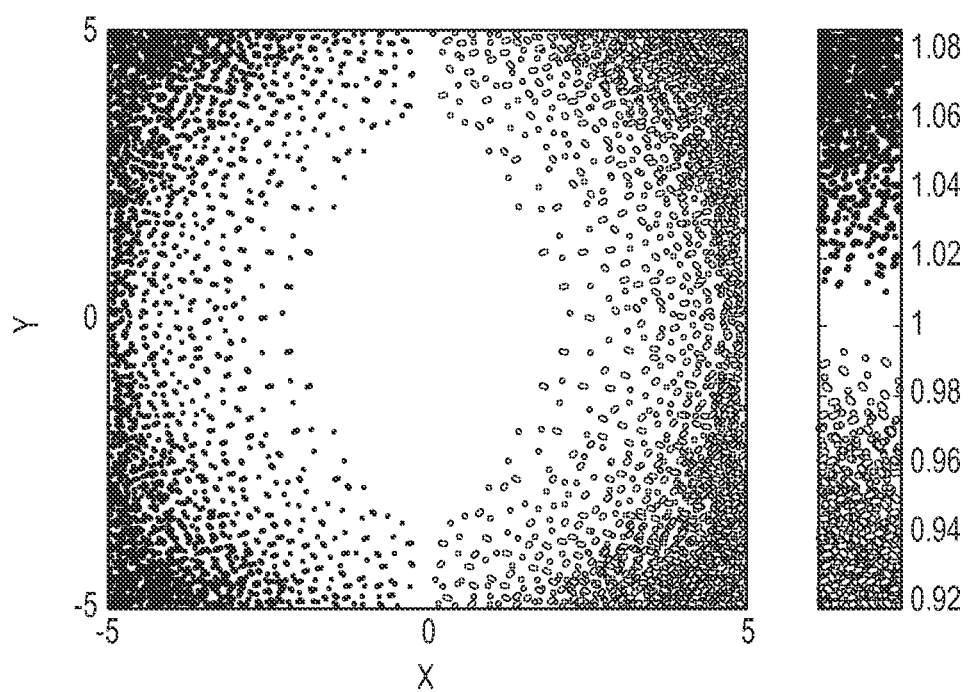

Using the procedures and formulas described herein an adjustment coefficient, $C_{asym}$, was calculated for an eye approximated by an ellipse having the following characteristics: a major axis of 11.2 mm (c=11.2 mm), a minor axis of 9.2 mm (a=9.2 mm), a tilted orientation of 5 degrees in the x direction, and no tilt in the y direction. The cosine asymmetry adjustment coefficient for the surface of the eye are shown in FIG. 12A. The resulting ablation errors that would result due to the tilt for a myopic ablation profile having no high-order aberrations can be calculated from the following formula:

$$errA = \left(\frac{C_{asym}}{C_0} - 1\right) \cdot A_{myo}$$

Figure 12B:
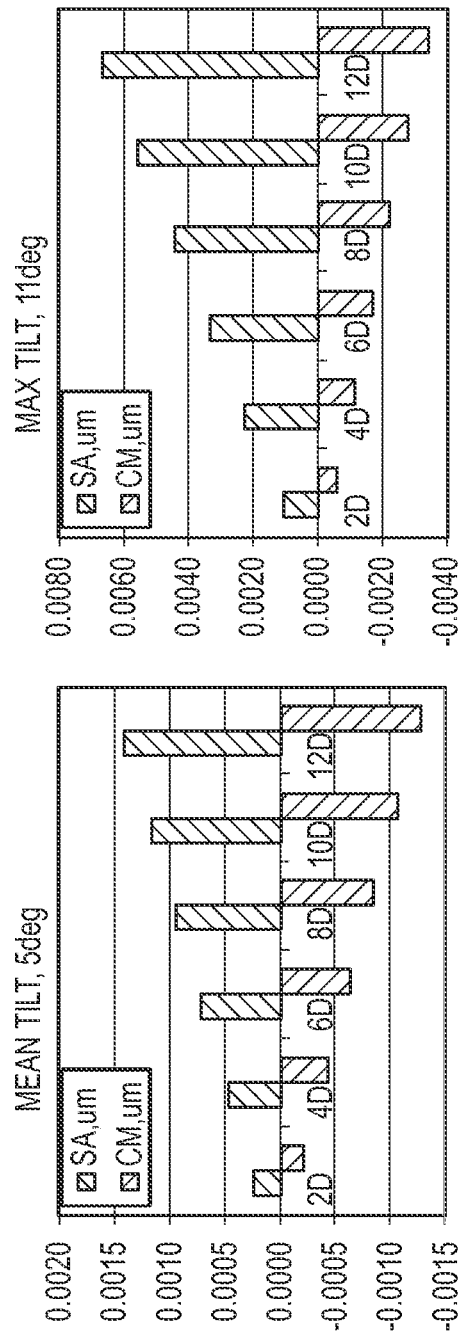

The term $A_{myo}$ indicates an ablation treatment profile for a myopic eye and the term $C_0$ indicates a cosine adjustment measure for an un-tilted ellipsoid (i.e., a cosine adjustment that would be applied to an un-tilted ellipsoid having the above characteristics). The estimated spherical aberrations and Coma that would result due to the ablation error are shown in FIG. 12B for different diopters of refractive correction of myopia patients. FIG. 12B shows that aberration effects due to eye tilt increases with increasing diopter values.

Using the ellipsoid with the above characteristics, the cosine values can be calculated for an un-tilted eye and compared with the values for a tilted left and right eye. The cosine values at the edge of an optical zone having a radius of 3 mm from the corneal vertex and an ablation zone having a radius of 4 mm from the corneal vertex are provided in FIG. 12C. As shown in FIG. 12C, when comparing the maximum values of the standard deviation bars, the tilt may change the slope cosine value by as much as 0.06.

The cosine value ratio of the tilted eyes (both left and right) to non-tilted eyes is shown in FIG. 12D. As shown in FIG. 12D, the tilted orientation of the eyes can vary the cosine value by 1-10%, which as described above may result in ablation treatment induced aberrations (spherical aberrations and/or coma) if not accounted for.

The methods and apparatuses of the present invention may be provided in one or more kits for such use. The kits may comprise a system for profiling an optical surface, such as an optical surface of an eye, and instructions for use. Optionally, such kits may further include any of the other system components described in relation to the present invention and any other materials or items relevant to the present invention. The instructions for use can set forth any of the methods as described herein.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

While the above provides a full and complete disclosure of the preferred embodiments of the present invention, various modifications, alternate constructions and equivalents may be employed as desired. Therefore, the above description and illustrations should not be construed as limiting the invention, which can be defined by the claims.

What is claimed is:

1. A method for treating an eye of a patient by ablation, the method comprising:
    obtaining a plurality of measurements of the eye;
    calculating an ellipsoid shape corresponding to an anterior corneal surface of the eye based on the plurality of measurements of the eye, the ellipsoid shape having an anterior portion, a major axis, and an apex, wherein the major axis intersects the anterior portion at the apex;
    determining a tilted orientation of the eye when the patient fixates on a target during a laser ablation procedure, wherein the tilted orientation includes a first tilt in a first direction and a second tilt in a second direction orthogonal to the first direction;
    determining an ablation treatment based on the ellipsoid shape and the tilted orientation; and
    controlling a pattern of laser pulses of a laser eye surgery system according to the ablation treatment determined.

2. The method of claim 1, wherein the tilted orientation comprises the major axis rotationally offset from an axis of a laser beam path.

3. The method of claim 1, wherein determining the tilted orientation comprises:
    determining a vertex of the ellipsoid, the vertex corresponding to a foremost point of the anterior corneal surface; and
    determining an offset between the apex and the vertex.

4. The method of claim 1, wherein determining the tilted orientation comprises:
    obtaining a topography measurement of the anterior corneal surface; and
    fitting the topography measurement on the ellipsoid shape to obtain the tilted orientation.

5. The method of claim 1, wherein determining the ellipsoid shape comprises determining a keratometry profile of the anterior corneal surface.

6. The method of claim 5, wherein the keratometry profile comprises a first curvature value, a second curvature value, and a torsional rotational angle.

7. The method of claim 1, further comprising determining one or more of the following:
    an energy level for a laser treatment device based on the ablation treatment; or
    an ablation time for the laser treatment device based on the ablation treatment.

8. The method of claim 1, further comprising determining a wavefront measurement of the eye, wherein the ablation treatment is determined based on the ellipsoid shape, the tilted orientation, and the wavefront measurement.

9. The method of claim 1, further comprising adjusting the ablation treatment based on a wavefront measurement of the eye.

10. A method for treating an eye of a patient by ablation, comprising:
    receiving, at a processor, a plurality of measurements of the eye; and
    executing, using the processor, computer executable code stored on a non-transitory computer readable medium, the computer executable code comprising instructions that when executed on the processor cause the processor to:
    calculate an ellipsoid shape corresponding to an anterior corneal surface of the eye based on the plurality of measurements received, the ellipsoid shape having an anterior portion, a major axis, and an apex, wherein the major axis intersects the anterior portion at the apex,
    determine a tilted orientation of the eye when the patient fixates on a target during a laser ablation procedure, wherein the tilted orientation includes a first tilt in a first direction and a second tilt in a second direction orthogonal to the first direction,
    determine ablation treatment based on the ellipsoid shape and the tilted orientation, and
    control a pattern of laser pulses of a laser eye surgery system according to the ablation treatment determined.

11. The method of claim 10, wherein the tilted orientation comprises the major axis rotationally offset from an axis of a laser beam path.

12. The method of claim 10, wherein the computer executable code comprises instructions that when executed on the processor further cause the processor to:
    determine a vertex of the ellipsoid, the vertex corresponding to a foremost point of the anterior corneal surface; and
    determine an offset between the apex and the vertex.

13. The method of claim 10, wherein the tilted orientation is based on a topography measurement of the anterior corneal surface that is fitted on the ellipsoid shape.

14. The method of claim 10, wherein the ellipsoid shape is based on a keratometry profile of the anterior corneal surface.

15. The method of claim 14, wherein the keratometry profile comprises a first curvature value, a second curvature value, and a torsional rotational angle.

16. The method of claim 10, wherein the computer executable code comprises instructions that when executed on the processor further cause the processor to:
    determine an energy level for a laser treatment device based on the ablation treatment;
    determine an ablation time for the laser treatment device based on the ablation treatment; or
    determine an energy level and an ablation time for the laser treatment device based on the ablation treatment.

17. The method of claim 10, further comprising receiving, at the processor, a wavefront measurement of the eye, wherein the computer executable code comprises instructions that when executed on the processor cause the processor to determine the ablation treatment based on the ellipsoid shape, the tilted orientation, and the wavefront measurement.

18. The method of claim 10, wherein the computer executable code comprises instructions that when executed on the processor cause the processor to further adjust the ablation treatment based on a wavefront measurement of the eye.

* * * * *